US006677503B1

(12) United States Patent
Bidney et al.

(10) Patent No.: US 6,677,503 B1
(45) Date of Patent: Jan. 13, 2004

(54) SUNFLOWER ANTI-PATHOGENE PROTEINS AND GENES AND THEIR USES

(75) Inventors: Dennis L. Bidney, Urbandale, IA (US); Jon Duvick, Des Moines, IA (US); Xu Hu, Urbandale, IA (US); Guihua Lu, Urbandale, IA (US); Oswald R. Crasta, Branford, CT (US)

(73) Assignees: Pioneer Hi-Bred International, Inc., Des Moines, IA (US); GuraGen Corporation, New Haven, CT (US)

( * ) Notice: Subject to any disclaimer, the term of this patent is extended or adjusted under 35 U.S.C. 154(b) by 0 days.

(21) Appl. No.: 09/589,733

(22) Filed: Jun. 8, 2000

Related U.S. Application Data
(60) Provisional application No. 60/140,646, filed on Jun. 23, 1999, and provisional application No. 60/162,904, filed on Nov. 1, 1999.

(51) Int. Cl.$^7$ .................. C12N 15/09; C12N 15/29; C12N 15/82; A01H 5/00; A01H 5/10

(52) U.S. Cl. .................. 800/279; 800/278; 800/298; 800/295; 800/322; 435/419; 435/468; 435/320.1; 536/23.2; 536/24.1; 536/23.6

(58) Field of Search ............................. 800/279, 278, 800/298, 295, 322; 536/23.2, 24.1, 23.6; 435/468, 419, 320.1

(56) References Cited

U.S. PATENT DOCUMENTS 5,801,028 A   9/1998   Bressan et al.

FOREIGN PATENT DOCUMENTS

| EP | 0332104 | 9/1989 |
|---|---|---|
| EP | 0392225 A2 | 10/1990 |
| EP | 0460753 A2 | 12/1991 |
| EP | 1 033 405 A | 9/2000 |
| WO | WO 92/17580 A1 | 10/1992 |
| WO | WO 93/05153 A | 3/1993 |
| WO | WO 94/08010 | 4/1994 |
| WO | WO 95/19443 A2 | 7/1995 |
| WO | WO 98/13478 A2 | 4/1998 |
| WO | WO 99/04012 | 1/1999 |
| WO | WO 99/50428 A | 10/1999 |
| WO | WO 00/11175 A | 3/2000 |
| WO | WO 00/11196 A | 3/2000 |
| WO | WO 00/68405 A | 11/2000 |
| WO | WO 00/78983 A2 | 12/2000 |

OTHER PUBLICATIONS

Ryals et al, "Systemic Acquired Resistance", Oct. 1996, The Plant Cell, vol. 8, pp. 1809–1819.*
Linthorst et al, "Constitutive Expression of Pathogenesis–Related Proteins PR–1, GRP and RP–S in Tobacco Has No Effect on Virus Infection", Mar. 1989, The Plant Cell, vol. 1, pp. 285–291.*
Lazar et al, "transforming Growth Factor x–Mutation of Aspartic Acid 47 and Leucine 48 Results in Different Biological Activities", Mar. 1988, Molecular and Cellular Biology vol. 8 No. 3, pp. 1247–1252.*
Broun et al, "Catalytic Plasticity of Fatty Acid Modification Enzymes Underlying Chemical Diversity of Plant Lipids", Nov. 1998, Science vol. 282, pp. 1315–1317.*
Datta et al., Database BIOSIS Accession No. PREV199903310941, "Over–Expression of the Cloned Rice Thaumatin–Like Protein (PR–5) Gene in Transgenic Rice Plants Enhances Environmental Friendly Resistance to Rhizoctonia Solani Causing Sheath Blight Disease," Abstract,*Theoretical and Applied Genetics*, May 1999, pp.
Dong et al., Database BIOSIS Accession No. PREV199799414966, "In Vivo and In Vitro Activity of Truncated Osmotin that is Secreted Into the Extracellular Matrix," *Plant Science*, pp. 123–1341, vol. 121, No. 2.
Hisashi et al, Database BIOSIS Accession No. PREV199799712464, "Purification and Characterization of Tobacco Pathogenesis–related Protein PR–5d, an Antifungal Thaumatin–like Protein," Abstract,*Plant and Cell Physiology* 1997, pp. 783–791, vol. 38, No. 7.
Jung et al., "Different Pathogenesis–Related–Proteins are Expressed in Sunflower (*Helianthus annuus* L..) in Response to Physical, Chemical and Stress Factors," *J. Plant Physiol.* 1995, pp. 153–160, vol. 145.
Jung et al., "Sunflower (*Helianthus annuus* L.) Pathogenesis–Related Proteins," *Plant Physiol.* 1993, pp. 873–880, vol. 101.
Loulakakis et al., Database EMBL Accession No. Y10992.
Loulakakis, "Nucleotide Sequence of a *Vitis vinifera* L. cDNA (Accession No. Y10992) Encoding for Osmotin–Like Protein (PGR97–064)," *Plant Physiol.* 1997, pp. 1464–1465, vol. 113.
Sato et al., "Synthesis and Secretion of Tobacco Neutral PR–5 Protein by Transgenic Tobacco and Yeast," *Biochem and Biophys Res. Commun*, Jun. 26, 1995, pp. 909–913, vol. 211, No. 3.
Sato et al., Database EMBL Accession No. D76437, NicotianaSylvestris DNA for Neutral PR–5 (Osmotin–Like Protein, PR–5d), Complete CDs, Jun. 25, 1996.
Sato et al., Database BIOSIS Accession No. PREV199699006022, "Ethylene–induced Gene Expression of Osmotin–like Protein, a Neutral Isoform of 'Tobacco RP–5, is Mediated by the AGCCGCDC cis–sequence," Abstract, *Plant and Cell Physiology*, 1996, pp. 249–255, vol. 37, No. 3.

(List continued on next page.)

Primary Examiner—Elizabeth F. McElwain
Assistant Examiner—Medina A. Ibrahim
(74) Attorney, Agent, or Firm—Alston & Bird LLP

(57) ABSTRACT

The invention relates to isolated sunflower nucleic acid sequences encoding a protein having antipathogenic activity, vectors, plant cells, plants and seeds comprising said nucleic acid sequences. The invention further relates to a method of transforming plants for increased resistance against plant pathogens.

14 Claims, 5 Drawing Sheets

OTHER PUBLICATIONS

Vigers et al., Thaumatin–like Pathogenesis–related Proteins are Antifungal,*Plant Science* 1992, pp. 155–161, vol. 83.

Zhu et al., "Activation of Two Osmotin–like Protein Genes by Abiotic Stimuli and Fungal Pathogen in Transgenic Potato Plants," *Plant Physiol.* 1995, pp. 929–937, vol. 108.

Ronald, P. C., "Resistance Gene Evolution," *Plant Biology* (1998), pp. 294–298, vol. 1.

Ceccardi, et al., "A Novel Protein Associated with Citrus Blight Has Sequence Similarities to Expansin," *Plant Molecular Biology* (1998) pp. 775–783, vol. 38.

Dittrich, H., et al., "Molecular Cloning, Expression, and Induction of Berbine Bridge Enzyme, an Enzyme Essential to the Formation of Benzophenanthridinealkaloids in the Response of Plants to Pathogenic Attack," *National Academy of Science*, 1991, pp. 9969–9973, vol. 88(1), Washington.

Domon, et al., "Nucleotide Sequence of Two Anther–Specific cDNAs from Sunflower (*Helianthus annus* L.)," *Plant Molecular Biology*, 1990, pp. 643–646, vol. 15, Nijoff Publishers, NL.

Domon, et al., "Exon Shuffling in Anther–Specific Genes from Sunflower", *Molecular & General Genetics*, 1994, pp. 312–317, vol. 244(2).

Facchini, et al., "Molecular Characterization of Berberine Bridge Enzyme Genes From Opium Poppy," *Plant Physiology*, 1996, pp. 1669–1677, vol. 112.

Hauschild, et al., "Isolation and Analysis of Gene bbe1 encoding the Berbine Bridge Enzyme from California Polly *Eschscolzia californica*," *Plant Molecular Biology*, 1998, pp. 473–478, vol. 36, Nijhoff Publishers, NL.

Hu, et al., "Cloning and Expression of a PR5–Like Protein from Arabidopsis: Inhibition of Fungal Growth by Bacterially Expressed Protein," *Plant Molecular Biology*, (1997) pp. 949–959, vol. 34.

Koiwa, et al., "Purification and Characterization of Tobacco Pathogenesis–Related Protein PR–5d, an Antifungal Thaumatin–Like Protein," *Plant and Cell Physiology*, 1997, pp. 783–791, vol. 38(7).

Liu, et al., "Osmotin Overexpression in Potato Delays Development of Disease Symptoms" *Proc. Natl. Acad. Sci. USA*, 1994, pp. 188–1892, vol. 91.

Liu, et al., "Fine Structure and Function of the Osmotin Gene Promoter," *Plant Molecular Biology*, 1995, pp. 1015–1026, vol. 29.

Regente, M., et al., "A Sunflower Leaf Antifungal Peptide Active Against *Sclerotinia sclerotiorum*" *Physiologia Plantarum*, 1997, pp. 178–182, vol. 100(1).

Thomma, et al. "Separate Jasmonate–Dependent and Salicylate–Dependent Defense–Response Pathways in Arabidopsis are Essential for Resistance to Distinct Microbial Pathogens", *Proc. Natl. Acad. Sci. USA*, 1998, :pp. 15107–15111, vol. 95.

Urdangarin, M., et al., "A Defensin Gene Expressed in Sunflower Inflorescence," *Plant Physiology and Biochemistry*, 2000, pp. 253–258, vol. 38(3), Paris.

Yamakawa, et al., "Spermine is a Salicylate–Independent Endogenous Inducer for Both Tobacco Acidic Pathogenesis–Related Proteins and Resistance against Tobacco Mosaic Virus Infection," *Plant Physiol.*, 1998, pp. 1213–1222, vol. 118.

Zhou, et al., "The Pto Kinase Conferring Resistance to Tomato Bacterial Speck Disease Interacts with Proteins that Bind a cis–element of Pathogenesis–Related Genes", *The EMBO Journal*, 1997, pp. 3207–3215, vol. 16(11).

BIOSIS Database for Accession No. PREV199799414966 (XP–002151844).

BIOSIS Database for Accession No. PREV199799712464 (XP002151842).

EMBL Database for Accession No. AC007060 (XP002160554).

EMBL Database for Accession No. X77993 (XP002160555).

NCBI Database Accession No. X15224.

NCBI Database Accession No. X12739.

NCBI Database Accession No. X15223.

NCBI Database Accession No. AAD03398.

NCBI Database Accession No. U03860.

NCBI Database Accession No. U30472.

NCBI Database Accession No. AC001229.

Gentzbittel et al. (1998), "Cloning of Molecular Markers for Disease Resistance in Sunflower, *Helianthus annuus* L.," *Chem. Appl. Genet.* 96:519–525.

U.S. patent application Ser. No. 09/685,292, Bao et al., filed Oct. 10, 2000.

\* cited by examiner

```
CLUSTAL W (1.7) multiple sequence alignment
P93621      MGLCKILSISSFLLTTLFFTSSYAATFNIQNHCSYTVWAAAVP-GGGMQLGSGQSWSLNV
O04708      MRFTTTLPILIPLLLSLLFTSTHAATFDILNKCTYTVWAAASP-GGGRRLDSGQSWTITV
P25096      ------------------------ARFEITNRCTYTVWAASVPVGGGVQLNPGQSWSVDV
PR5-1sun    ---MTTSTLPTFLLLAILFHYTNAAVFTIRNNCPYTVWAGAVP-GGGRQLNSGQTWSLTV
Q01591      -----------FFFLLAFVTYTYAATFEVRNNCPYTVWAASTPIGGGRRLDRGQTWVINA
P50701      ---MAYLRSSFVFFLLAFVTYTYAATIEVRNNCPYTVWAASTPIGGGRRLDRGQTWVINA
                       *  : *.*.*****.: * *** :*. **:*  :.

P93621      NAGTTGARVWGRTNCNFDASGNGKCETGDCGGLLQCTAYGTPPNTLAEFALNQFSNLDFF
O04708      NPGTTNARIWGRTSCTFDANGRGKCETGDCNGLLECQGYGSPPNTLAEFALNQPNNLDYI
P25096      PAGTKGARVWARTGCNFDGSGRGGCQTGDCGGVLDCKAYGAPPNTLAEYGLNGFNNLDFF
PR5-1sun    AAGTAGARIWPRTNCNFDGSGRGRCQTGDCNGLLQCQNYGTPPNTLAEYALNQFNNLDFF
Q01591      PRGTKMARIWGRTNCNFDGDGRGSCQTGDCGGVLQCTGWGKPPNTLAEYALDQFSNLDFW
P50701      PRGTKMARIWGRTNCNFDGAGRGSCQTGDCGGVLQCTGWGKPPNTLAEYALDQFSNLDFW
            **   **:* **.*.**. *.*  :****:*:*   :* *******:.*: . .***:

P93621      FDISLVDGFNVPMAFNPT--SNGCTRGISCTADIVGECPAALKTTGGCNNPCTVFKTDEY
O04708      IDISLVDGFNIPMDFS------GC-RGIQCSVDINGQCPSELKAPGGCNNPCTVFKTNEY
P25096      FDISLVDGFNVPMDFSPT--SNGCTRGISCTADINGQCPSELKTQGGCNNPCTVFKTDQY
PR5-1sun    FDISLVDGFNVPMVFRPN--SNGCTRGISCTADINGQCPGELRAPGGCNNPCTVYKTDQY
Q01591      WDISLVDGFNIPMTFAPTNPSGGKCHAIHCTANINGECPGSLRVPGGCNNPCTTFGGQQY
P50701      WDISLVDGFNIPMTFAPTNPSGGKCHAIHCTANINGECPGSLRVPGGCNNPCTTFGGQQY
             *********:** *       * :  *  *:* *:**. *:  ********. :  :*

P93621      CCNSG--SCNATTYSEFFKTRCPDAYSYPKDDQTSTFTCPAG-TNYEVIFCP--------
O04708      CCTDGPGSCGPTTYSKFFKDRCPDAYSYPQDDKTSLFTCPSG-TNYKVTFCP--------
P25096      CCNSG--SCGPTDYSRFFKQRCPDAYSYPKDDPPSTFTCNGG-TDYRVVFCP--------
PR5-1sun    CCNSG--NCGPTDLSRFFKTRCPDAYSYPKDDPTSTFTCPGG-TNYDVIFCP--------
Q01591      CCTQG--PCGPTDLSRFFKQRCPDAYSYPQDDPTSTFTCPSGSTNYRVVFCPNGVTSPNF
P50701      CCTQG--PCGPTDLSRFFKQRCPDAYSYPQDDPTSTFTCPSGSTNYRVVFCPNGVTSPNF
            **..*    *.** .*.*** ********:** .*.***..  .*  *.***

P93621      ------------
O04708      ------------
P25096      ------------
PR5-1sun    ------------
Q01591      PLEMPSSDEEAK
P50701      PLEMPASDEEAK
```

FIG. 2.

```
CLUSTAL W (1.7) multiple sequence alignment
P30986     -MENKTPIFFSLSIFLS------LLNCALGG--ND--LLSCLTFNGVRNHTV---FSADS
P93479     MMCRSLTLRFFLFIVL-------LQTCVRGGDVNDNLLSSCLNSHGVHNFTT---LSTDT
Sunf-19    ---METSILTLLLLLLS------TQSSATSRSITDR-FIQCLHDRADPSFPITGEVYTPG
Sunf-15    ---MQTSILTLLLLLLS------TQSSATSRSITDR-FIQCLHDRADPSFPITGEVYTPG
BBE        --MNNSRSVFLLVLALSFCVSFGALSSIFDVTSTSEDFITCLQSNSNNVTTISQLVFTPA
                   *   *                     **

P30986     DSDFNRFLHLSIQNPLFQNSLISKPSAIILPGSKEELSNTIRCIRKGSWTIRLRSGGHSY
P93479     NSDYFKLLHASMQNPLFAKPTVSKPSFIVMPGSKEELSSTVHCCTRESWTIRLRSGGHSY
Sunf-19    NSSFPTVLQNYIRNLRFNETTTPKPFLIITAEHVSHIQAAVVCGKQNRLLLKTRSGGHDY
Sunf-15    NSSFPTVLQNYIRNLRFNETTTPKPFLIITAEHVSHIQAAVVCGKQNRLLLKTRSGGHDY
BBE        NTSYIPIWQAAADPIRFNKSYIPKPSVIVTPTDETQIQTALLCAKKHGYEFRIRDGGHDF
                      *   **  *              **         **.***.

P30986     EGLSYTSDT--PFILIDLMNLNRVSIDLESETAWVESGSTLGELYYAITESSSKLGFTAG
P93479     EGLSYTADT--PFVIVDMMNLNRISIDVLSETAWVESGATLGELYYAIAQSTDTLGFTAG
Sunf-19    EGLSYLTNTNQPFFIVDMFNLRSINVDIEQETAWVQAGATLGEVYYRIAEKSNKHGFPAG
Sunf-15    EGLSYLTNTNQPFFIVDMFNLRSINIDIEQETAWVQAGATLGEVYYRIAEKSNKHGFPAG
BBE        EGNSYTANA--PFVMLDLVNMRAIEINVENRTALVQGGALLGELYYTISQKTDTLYFPAG
           ** **     **. **.*.       .***.* ***:** ..    *.**

P30986     WCPTVGTFFGISGGGFGMMSRKYGLAADNVVDAILIDANGAILDRQAMGEDVFWAIRGGG
P93479     WCPTVGSGGHISGGGFGMMSRKYGLAADNVVDAILIDSNGAILDREKMGDDVFWAIRGGG
Sunf-19    VCPTVGVGGHFSGGGYGNLMRKYGLSVDNIVDAQIIDVNGKLLDRKSMGEDLFWAYTGGG
Sunf-15    VCPTVGVGGHFSGGGYGNLMRKYGLSVDNIVDAQIIDVNGKLLDRKSMGEDLFWAITGGG
BBE        IWAGVGVSGFLSGGGYGNLLRKYGLGADNVLDIRFMDVNGNILDRKSMGEDLFWALRGGG
            *   *  ***** *  ******.    *****  .***  ****   ***  ***

P30986     GGVWGAIYAWKIKLLPVPEDVTVFRVTKNVAIDEATSLLHKWQFVAEELEED------FT
P93479     GGVWGAIYAWKIKLLPVPEDLTVFRVTKNVGIEDASSLLHKWQYVADELDED------FT
Sunf-19    GVSFGVVLAYKIKLVRVPEVVTVFTIER-REEQNLSTIAERWVQVADKLDRDLFL--RMT
Sunf-15    GVSFGVVLAYKIKLVRVPEVVTVFTIER-REEQNLSTIAERWVQVADKLDRDLFL--RMT
BBE        ASSFGIVLQWKLNLVPVPERVTLFSVSY-TLEQGATDIFHKYQYVLPKFDRDLLIRVQLN
            *   *  **  * ***  * *                  *    *

P30986     LSVLGGADE-KQVWLTMLGFHFGLKTVAKSTFDLLFPELGLVEEDYLEMSWGESFAYLAG
P93479     VSVLGGVNG-NDAWLMFLGLHLGRKDAAKTIIDEKFPELGLVDKEFQEMSWGESMAFLSG
Sunf-19    FSVINDTNGGKTVRAIFPTLYLGNSRNLVTLLNKDFPELGLQESDCTEMSWVESVLYYTG
Sunf-15    FSVINDTNGGKTVRAIFPTLYLGNSRNLVTLLNKDFPELGLQESDCTENSWVESVLYYTG
BBE        TEYIGNTTQ-KTVRILFHGIYQGNIDTLLPLLNQSFPELNVTREVCQEVRMVQTTLEFGG
             .     .   *       . *            ****.     * .

P30986     LETVSQLNNRFLKFDERA--FKTKVDLTKEPLPSKAFYGLLERLSKEPN-GFIALNGFGG
P93479     LDTISELNNRFLKFDERA--FKTKVDFTKVSVPLNVFRHALEMLSEQPG-GFIALNGFGG
Sunf-19    FPSGTPTTALLSRTPQRLNPFKIKSDYVQNPISKRQFEFIFERMKELEN-QMLAFNPYGG
Sunf-15    FPSGTPTTALLSRTPQRLNPFKIKSDYVQNPISKRQFEFIFERLKELEN-QMLAFNPYGG
BBE        FNISTPTSVLANRSAIPKLSFKGKSDYVRTPIPRSGLRKLWRKMFENDNSQTLFMYTFGG
                          **  * ,     , *              **
```

FIG. 3A.

```
P30986    QMSKISSDFTPFPHRSGTRLMVEYIVAWNQSEQKK---KTEFLDWLEKVYEFMKPFVSKN
P93479    KMSEISTDFTPFPHRKGTKLMFEYIIAWNQDEESK---IGEFSEWLAKFYDYLEPFVSKE
Sunf-19   RMSEISEFAKPFPHRSGNIAKIQYEVNWEDLSDEA---ENRYLNFTRLMYDYMTPFVSKN
Sunf-15   RMSEISEFAKPFPHRSGNIAKIQYEVNWEDLSDEA---ENRYLNFTRLMYDYMTPFVSKN
BBE       KMEEYSDTAIPYPHRAGVLYQVFKRVDFVDQPSDKTLISLRRLAWLRSFDKTLEPYVTSN
          :*.: *    *:*** *   ,  : : :           ,   :    , : *:*: .:

P30986    PRLGYVNHIDLDLGGIDWGNKTVVNNAIEISRSWGESYF-LSNYERLIRAKTLIDPNNVF
P93479    PRVGYVNHIDLDIGGIDWRNKSSTTNAVEIARNWGERYF-SSNYERLVKAKTLIDPNNVF
Sunf-19   PREAFLNYRDLDIG-INSHGR----NAYTEGMVYGHKYFKETNYKRLVSVKTKVDPDNFF
Sunf-15   PRKAFLNYRDLDIG-INSHGR----NAYTEGMVYGHKYFKETNYKRLVSVKTKVDPDNFF
BBE       PREAYMNYNDLDLG--FDS------AAYEEASEWGERYWKRENFKKLIRIKAKVDPENFF
          ** ,::*: *** :*         *   .  :*, *:   *::*:  *:  :**:*.*

P30986    NHPQSIPPMANFD--YLEKTLGSDGGEVVI
P93479    NGPQSIPPMMKFEEIYMLKEL---------
Sunf-19   RNEQSIPTLSS-------------------
Sunf-15   RNEQSIPTLSS-------------------
BBE       RHPQSIPVFSRPLSDM--------------
          .: ****  :
```

FIG. 3B.

```
CLUSTAL W (1.7) multiple sequence alignment
P30230    MAKFASIIVLLFVALVVFAAFEEPTMVEAQKLCQRPSGTWSGVCGNNNACKNQCIRLEKA
P30231    ----------------------------QKLCERPSGTWSGVCGNNNACKNQCINLEKA
P30224    MAKSATIVTLFFAALVFFAALEAPMVVEAQKLCERPSGTWSGVCGNSNACKNQCINLEKA
defensin  MAKISVAFNAFLLLLFVLAISEIGSVKG--ELCEKASQTWSGTCGKTKHCDDQCKSWEGA
Q01784    MEKKSLAALSFLLLLVLFVAQEIVVTEA--NTCEHLADTYRGVCFTNASCDDHCKNKAHL
                              : *:: : *: *.* ,. *.::*

P30230    RHGSCNYVFPAHKCICYFPC----------------------------
P30231    RHGSCNYVFPAHKCICYFPC----------------------------
P30224    RHGSCNYVFPAHKCICYFPC----------------------------
defensin  AHGACHVRDGKHMCFCYFNCSKAQKLAQDKLRAEELAKEKIEPEKATAKP
Q01784    ISGTCHD----WKCFCTQNC----------------------------
              *:*:       *:*   *
```

FIG. 4.

SUNFLOWER ANTI-PATHOGENE PROTEINS AND GENES AND THEIR USES

CROSS-REFERENCE-TO RELATED APPLICATIONS

The present application claims the benefit of U.S. Provisional Application Serial No. 60/140,646, filed Jun. 23, 1999, and U.S. Provisional Application No. 60/162,904, filed Nov. 1,1999, both entitled "Sunflower Anti-Pathogenic Proteins and Genes and Their Uses," the contents of which are herein incorporated by reference in their entirety.

FIELD OF THE INVENTION

The invention relates to nucleotide sequences and proteins for anti-pathogenic agents and their uses, particularly the genetic manipulation of plant with genes that enhance disease resistance. Promoter sequences are also provided.

BACKGROUND OF THE INVENTION

Plant diseases are often a serious limitation on agricultural productivity and have therefore influenced the history and development of agricultural practices. Only recently have Mendelian genes controlling disease resistance been isolated, and elucidation of their biochemical functions remains a major challenge.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight.

Mendelian genetics of resistance to disease in plants is well known. Resistance is often controlled by a single gene, either dominant, semidominant, or recessive. In some instances, multigenes are involved. However, the biochemical mechanisms for gene products involved in plant resistance are known in only a few model cases.

Among the causal agents of infectious diseases of crop plants, phytopathogenic fungi play the dominant role not only by causing devastating epidemics, but also through the less spectacular although persistent and significant annual crop yield losses that have made fungal pathogens a serious economic factor. All of the species of flowering plants are attacked by pathogenic fungi. Generally, however, a single plant species can be host to only a few fungal species, and similarly, most fungi have a limited host range.

To colonize plants, fungal microorganisms have evolved strategies to invade plant tissue, to optimize growth in the plant, and to propagate. Bacteria and viruses, as well as some opportunistic fungal parasites, often depend on natural openings or wounds for invasion. In contrast, many true phytopathogenic fungi have evolved mechanisms to actively traverse the plant's outer structural barriers, the cuticle and the epidermal cell wall. To gain entrance, fungi generally secrete a cocktail of hydrolytic enzymes.

Despite the large number of microorganisms capable of causing disease, most plants are resistant to any given pathogen. The defense mechanisms utilized by plants can take many different forms, ranging from passive mechanical or preformed chemical barriers, which provide non-specific protection against a wide range of organisms, to move more active host-specific responses that provide host-or varietal-specific These genes have been employed in breeding programs upon discovery.

A hypersensitive response (HR) that is elaborated in response to invasion by all classes of pathogens is the most common feature associated with active host resistance. In most cases, activation of the HR leads to the death of cells at the infection site, which results in the restriction of the pathogen to small areas immediately surrounding the initially infected cells. At the whole plant level, the HR is manifested as small necrotic lesions. The number of cells affected by the HR is only a small fraction of the total in the plant, so this response obviously contributes to the survival of plants undergoing pathogen attack.

In plants, robust defense responses to invading phytopathogens often conform to a gene-for-gene relationship. Resistance to a pathogen is only observed when the pathogen carries a specific avirulence (avr) gene and the plant carries a corresponding resistance (R) gene. Because avr-R gene-for-gene relationships are observed in many plant-pathogens systems and are accompanied by a characteristic set of defense responses, a common molecular mechanism avr-R gene mediated resistance has been postulated. Thus, disease resistance results from the expression of a resistance gene in the plant and a corresponding avirulence gene in the pathogen and is often associated with the rapid, localized cell death of the hypersensitive response. R genes that respond to specific bacteria, fungal, or viral pathogens have been isolated from a variety of plant species and several appear to encode cytoplasmic proteins. It has been unclear how such proteins could recognize an extracellular pathogen. Many strategies for plant disease control have been attempted. Resistant cultivars has been selected or developed by plant breeders for disease control. Resistance is especially important for major crops such as the cereals, sugar cane, potato, and soybean. The limitation in use of disease resistance in modern agriculture is adaptability by pathogens to overcome resistance.

The development of new strategies to control diseases is the primary purpose of research on plant/pathogen interactions. These include, for example, the identification of essential pathogen virulence factors and the development of means to block them, or the transfer of resistance genes into crop plants from unrelated species. An additional benefit is a better understanding of the physiology of the healthy plant through a study of the metabolic disturbances caused by plant pathogens.

SUMMARY OF THE INVENTION

Anti-pathogenic compositions and methods for their use are provided. The compositions comprise anti-pathogenic proteins and their corresponding genes and regulatory regions. Particularly, sunflower PR5-1, defensin, and berberine bridge enzyme (BBE) homologues, and fragments and variants thereof, are provided.

The compositions are useful in protecting a plant from invading pathogenic organisms. One method involves stably transforming a plant with a nucleotide sequence of the invention to engineer broad spectrum disease resistance in the plant. The nucleotide sequences will be expressed from a promoter capable of driving expression of a gene in a plant cell. A second method involves controlling plant pathogens by applying an effective amount of an anti-pathogenic protein or composition of the invention to the environment of the pathogens. Additionally, the nucleotide sequences of the invention are useful as genetic markers in disease resistance breeding programs.

Promoters of the genes of the invention find use as disease or pathogen-inducible promoters. Such promoters may be used to express other coding regions, particularly other anti-pathogenic genes, including disease and insect resistance genes.

The compositions of the invention additionally find use in agricultural and pharmaceutical compositions as antifungal and antimicrobial agents. For agricultural purposes, the compositions may be used in sprays for control of plant disease. As pharmaceutical compositions, the agents are useful for antibacterial and antimicrobial treatments.

The methods of the invention find use in controlling pests, including fungal pathogens, viruses, nematodes, insects, and the like. Transformed plants, plant cells, plant tissues, and seeds, as well as methods for making such transformed compositions are additionally provided.

BRIEF DESCRIPTION OF THE DRAWINGS

FIG. 2 depicts an alignment of the amino acid sequence of PR5-1 (SEQ ID:13from sunflower with other PR5 or osmatin-like proteins from grape, (Swiss-Prot Accession Nos. P93621, SEQ ID: 10; and 004708, SEQ ID: 11); soybean, (Swiss-Prot Accession No. P25096, SEQ ID:12); tomato, (Swiss-Prot Accession No. Q01591, SEQ ID:14); and potato, (Swiss-Prot Accession No. P50701,SEQ ID:15). A star indicates that the amino acid at that position is conserved for all aligned sequences, and a dash denotes gaps in alignment.

FIG. 3 depicts an alignment of the amino acid sequence of a BBE (SEQ ID:20) from sunflower with other BBE homologues and two possible sunflower carbohydrate oxidases. Sunflower-15 (SEQ ID:17) and -19 (SEQ ID:16) sequences were reported in WO 98/13478. Other BBE sequences include a reticuline oxidase precursor from California poppy, (Swiss-Prot Accession No. P30986, SEQ ID: 19) and a BBE from opium poppy, (Swiss-Prot Accession No. P93479, SEQ ID: 18).

FIG. 4 depicts an alignment of the amino acid sequence of a sunflower defensin (SEQ ID:24)with other antifungal defensins from garden pea (Swiss-Prot Accession No. Q01784, SEQ ID:25), white mustard (Swiss-Prot Accession No. P30231, SEQ ID:22), radish (Swiss-Prot Accession No. P30230, SEQ ID:21) and Arabidopsis (Swiss-Prot Accession No. P30224,.SEQ ID:23).

DETAILED DESCRIPTION OF THE INVENTION

Figure 1:
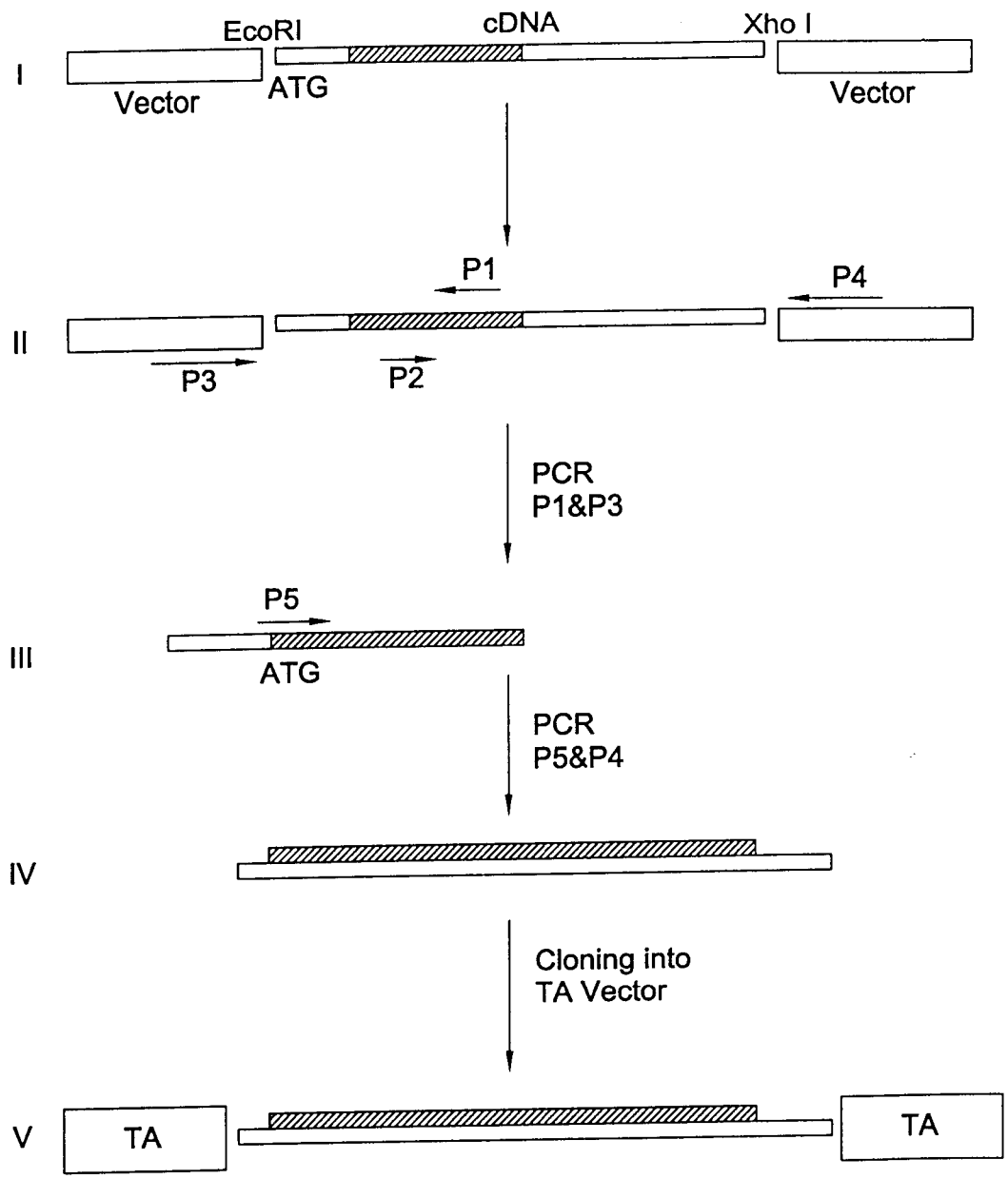
FIG. 1 depicts the cDNA cloning strategy. (I) Sunflower cDNA libraries were directionally constructed into pBluescript phagemid using a ZAP-cDNA synthesis kit from Stratagene; (II) oligonucleotide primers (P1 and P3) were used to amplify the 5' end of a target gene by a rapid amplification of cDNA ends (RACE) method. PCR and the 3'end of the gene were amplified with P2 and P4 primers; (111) P5 primer was designed at the putative start codon (ATG) or upstream the start codon in order to clone fulllength cDNA; (IV) the full-length cDNA of the target gene were amplified by PCR with P5 and P4 primers; and (V) the expected full-length cDNA was inserted into TA vector (Invitrogen) for sequencing. Shaded areas represent cloned regions.

Compositions and methods for controlling pathogenic agents are provided. The anti-pathogenic compositions comprise sunflower genes, including their promoters, and proteins. Particularly, the sunflower genes and proteins are selected from PR5-1, defensin, and berberine bridge enzyme (BBE). Accordingly, the methods are also useful in protecting plants against fungal pathogens, viruses, nematodes, insects and the like. Additionally, the compositions can be used in formulation use for their antimicrobial activities.

Additionally, the present invention provides for isolated nucleic acid molecules comprising nucleotide sequences for plant promoters shown in SEQ ID:7, SEQ ID:8, and SEQ ID:9; for nucleotide sequences encoding the amino acid sequences shown in SEQ ID: 1, SEQ ID:2, and SEQ ID:3; the nucleic acid molecules deposited in a bacterial host as Patent Deposit Nos. PTA-67, PTA-73, PTA-75, respectively; and the nucleic acid molecule deposited as Patent Deposit No. PTA-560 which comprises the nucleotide sequence shown in SEQ ID:9. Further provided are polypeptides having an amino acid sequence encoded by a nucleic acid molecule described herein, for example those set forth in SEQ ID:4, SEQ ID:5, and SEQ ID:6 those deposited as Patent Deposit Nos. PTA-67, PTA-73, PTA-75, respectively, and fragments and variants thereof.

Plasmids containing the promoter sequences and gene nucleotide sequences of the invention were deposited with the Patent Depository of the American Type Culture Collection, Manassas, Va. The following plasmids were deposited: May 13, 1999, pHp 15383 containing BBE cDNA; May 13, 1999, pHp 15384 containing BBE promoter sequence; May 13, 1999, pHp 15385 containing defensin cDNA; Aug. 31, 1999, pHp 16125 containing defensin promoter sequence; May 13, 1999, pHp 15395 containing PR5-1 promoter sequences; and May 14, 1999, pHp 15393 containing PR5-1 cDNA; and assigned Patent Deposit Nos. PTA-73; PTA-74, PTA-75, PTA-560, PTA-76, PTA-67, respectively. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

As indicated, the sequences of the invention find use as antifungal agents. Thus, the genes can be used to engineer plants for broad spectrum disease resistance. In this manner, the sequences can be used alone or in combination with each other and/or with other known disease resistance genes.

Additionally, the sequences can be used as markers in studying defense signal pathways and in disease resistance breeding programs. The sequences can also be used as baits to isolate other signaling components in defense/resistance responsiveness and to isolate the corresponding promoter. See, generally, Sambrook et al. (1989) *Molecular Cloning: A Laboratory Manual* (2d ed.), Cold Spring Harbor Laboratory Press, Plainview, N.Y.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably, culture medium represents less than about 30%, 20%, 10%, or 5% (by dry weight) of chemical precursors or non-protein of interest chemicals.

By "anti-pathogenic compositions" is intended that the compositions of the invention are capable of suppressing, controlling, and/or killing the invading pathogenic organism.

By "disease resistance" is intended that the plants avoid the disease symptoms that are the outcome of plant-pathogen interactions. That is, pathogens are prevented from causing plant diseases and the associated disease symptoms. The methods of the invention can be utilized to protect plants from disease, particularly those diseases that are caused by plant pathogens.

The compositions of the invention include isolated nucleic acid molecules comprising the promoter nucleotide sequences set forth in SEQ ID:7, SEQ ID:8 and SEQ ID:9. By "promoter" is intended a regulatory, region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5'untranslated region upstream from the particular promoter regions identified herein. Thus, for example, the promoter regions disclosed herein may further comprise upstream regulatory elements that confer tissue-preferred expression of any heterologous nucleotide sequence operably linked to one of the disclosed promoter sequences. See particularly Australian Patent No. AU-A-5 77751/94 and U.S. Pat. Nos. 5,466,785 and 5,635,618. Generally with the promoter sequences of the invention, the pattern of expression will be inducible.

The inducible promoter sequences of the present invention, when assembled within a DNA construct such that the promoter is operably linked to a nucleotide sequence of interest, enable expression of the nucleotide sequences in the cells of a plant stably transformed with this DNA construct. The nucleotide sequence of interest encompasses both homologous and heterologous sequences. By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. Choice of the promoter sequence will determine when and where within the organism the heterologous nucleotide sequence is expressed. Where gene expression in response to a stimulus is desired, an inducible promoter of the invention is the regulatory element of choice. When using an inducible promoter, expression of the nucleotide sequence is initiated in cells in response to a stimulus. By "stimulus" is intended a chemical, which may be applied externally or may accumulate in response to another external stimulus; a pathogen, which may, for example, induce expression as a result of invading a plant cell; or other factor such as environmental stresses, including but not limited to, drought, temperature, and salinity.

Compositions of the invention also include the nucleotide sequences for three sunflower genes: a sunflower PR5 homologue as set forth in SEQ ID:4; a sunflower defensin homologue as set forth in SEQ ID:6; and, a sunflower BBE homologue as set forth in SEQ ID:5, and the corresponding amino acid sequences for the proteins encoded thereby as set forth in,SEQ ID: 1, SEQ ID:3 and SEQ ID:2, respectively. These gene sequences may be assembled into a DNA construct such that the gene is operably linked to a promoter that drives expression of a coding sequence in a plant cell. Plants stably transformed with this DNA construct express, either in a constitutive or inducible manner, a protein of the invention. Expression of this protein creates or enhances disease resistance in the transformed plant.

BBE [9S0reticuline:oxygen oxidoreductase (methylene-bridge-forming), EC 1.5.3.9] is a covalently flavinylated oxidase that is a key enzyme in benzophenanthridine alkaloid biosynthesis in plants (Kutchan et al (1995) *J. Biol. Chem.* 270:24475–24481; Blechert et al. (1995) *Proc. Natl. Acad. Sci. USA* 92:4099–4105; Dittrich et al. (1991) *Proc. Natl. Acad. Sci. USA* 88:9969–9973; Chou et al. (1998) *Plant J.* 15:289–300). Members of the alkaloid family are known to have potent pharmacological activities. Berberine, for example, is currently used as an antibacterial treatment for eye infections in Europe and for intestinal infections in the far East. The benzophenanthridine alkaloid, sanguimarine, is an antimicrobial used in the treatment of peridontal disease in both the United States and Europe (Kutchan et al. (1995) *J. Biol. Chem.* 270:24475–24481). In addition, BBE has anti-Phlytophthora and anti-Pythium activity, as well as carbohydrate oxidase activity (WO 98/13478). The BBE-transgenic plants of the invention have enhanced resistance to pathogens. BBE and several other enzymes in the defense pathway are induced by elicitors. See for example Blechert et al. (1995) *Proc. Natl. Acad. Sci. USA* 92:4099–4105; Dittrich et al. (1991) *Proc. Natl. Acad. Sci. USA* 88:9969–9973.

A sunflower BBE is disclosed that is regulated by oxalate oxidase (oxox) expression and Sclerotinia infection. The cDNA (SEQ ID:5) and promoter (SEQ ID:8) sequences of sunflower BBE are provided. In addition, expression of this BBE in sunflower was up-regulated by oxalic acid, $H_2O_2$, salicylic acid (SA) and jasmonic acid (JA).

Pathogenesis-related protein-5 (PR5) is one of the 9 classes of PR proteins. PR5 shares sequence similarity with osmotin, thaumatin, and zeamatin proteins (Hu et al. (1997) *Plant Mol. Biol.* 34:949–959; Ryals et al (1996) *Plant Cell* 8:1809–1819). PR5 proteins have been characterized from a wide range of plant species in both dicotyledonous and monocotyledonous plants. Although the biological function of PR5 proteins has yet to be established, members of this group have been shown to have antifungal activities against a broad range of fungal pathogens (Hu et al. (1997) *Plant Mol. Biol.* 34:949–959; Ryals et al. (1996) *Plant Cell* 8:1809–1819); Liu et al. (1994) *Proc. Natl. Acad. Sci. USA* 91:1888–1892; Liu et al. (1995) *Plant Mol. Biol.* 29:1015–1026; Zhu et al. (I1995) *Plant Physiol.* 108:929–937). In Arabidiospsis, the induction of PR5 is SA-dependent. The sunflower PR5-1 gene disclosed herein was regulated by oxox expression and Sclerotinia-infection. The sunflower PR5-1 promoter contains potential pathogen-responsive cis-elements, such as an MRE (MYB recognition element).

Defensins are one class among the numerous types of Cys-rich antimicrobial polypeptides, which differ in length, number of cysteine bonds, or folding pattern (Bomann, H.G. (1995) *Annu. Rev. Immunol.* 13:61–92). Like cecropins, insect defensins are produced in a pathogen-inducible manner by the insect fat body and secreted in the hemolymph (Huffmann et al. (1992) *Innmuniol Today* 13:411–415). Mammalian defensins are produced by various specialized cells in the mammalian body (Lehrer et al. (I 993)*Annu. Rev. Immunol.* 11: 105–128; Ganz et al. (I1994) *Curr. Opin. Immunol.* 6:584–589). The structural and functional properties of plant defensins resemble those of insect and mammalian defensins (Terras et al. (1995) *Plant Cell* 7:573–588; Broekaer et al. (1995) *Plant Physiol.* 108:1353–1358). Plant defensins inhibit the growth of a broad range of fungi at micromolar concentrations by inhibiting hyphal elongation or inhibiting hyphal extension (Broekaer et al. (I1995) *Plant Physiol.* 108:1353–1358).

Plant defensins are important components of the defense system in plants. They are located at the periphery of different organs and are induced by pathogens. A sunflower cDNA was isolated that encodes a defensin peptide (SEQ ID:6). This defensin gene was up regulated by Sclerotinia infection, oxox expression, oxalic acid, $H_2O_2$ and SA as well as jasmonic acid. In general, plant defensin genes such as Arabidopsis PDF1.2 and a radish defensin are induced by pathogens via an SA-independent and JA-dependent pathway (Thomma et al.) *Proc. Natl. Acad. Sci. USA* 95:15107–1511 1; Terras et al. (1995) *Plant Cell* 7:573–588;'Terra et al. (1988) *Planta* 206:117–124). The sunflower defensin gene appears to be the only defensin that is regulated via a SA-dependent pathway. The sunflower defensin promoter contains potential pathogen responsive cis-elements, such as W-boxes and G-boxes.

The proteins of the invention may be altered in various ways including amino acid substitutions, deletions, truncations, and insertions. Methods for such manipulations are generally known in the art. For example, amino acid sequence variants of the proteins can be prepared by mutations in the DNA. Methods for mutagenesis and nucleotide sequence alterations are well-known in the art. See, for example, Kunkel, T. (1 985) *Proc. Natl. Acad. Sci. USA* 82:488–492; Kunkel et al. (1987) *Methods in Enzymol.* 154:367–382; U.S. Pat. No. 4,873,192; Walker et al. (1983) (eds.) *Techniques in Molecular Biology*, MacMillan Publishing Company, N.Y. and the references cited therein. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired defense activation activity. Obviously, the mutations that will be made in the DNA encoding the variant must not place the sequence out of reading frame and preferably will not create complementary regions that could produce secondary mRNA structure. See, for example, EP Patent Application Publication No. 75,444.

Fragments and variants of these-native nucleotide and amino acid sequences are also encompassed by the present invention. By "fragment" is intended a portion of the nucleotide or amino acid sequence. Fragments of a promoter nucleotide sequence may retain their regulatory activity. Thus, for example, less than the entire promoter sequences disclosed herein may be utilized to drive expression of an operably linked nucleotide sequence of interest, such as a nucleotide sequence encoding a heterologous protein. It is within skill in the art to determine whether such fragments decrease expression levels or alter the nature of expression; i.e., and constitutive or inducible expression. Alternatively, fragments of a promoter nucleotide sequence that are useful as hybridization probes, such as described below, generally do not retain this regulatory activity.

Nucleic acid molecules that are fragments of a promoter nucleotide sequence comprise at least 15, 20, 25, 30, 35, 40, 45, 50, 75, 100, 325, 350, 375, 400, 425, 450, or 500 nucleotides, or up to the number of nucleotides present in the full-length promoter nucleotide sequence set forth in SEQ ID: 7, 8, and 9. Fragments of a promoter sequence that retain their regulatory activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are also encompassed by the compositions of the present invention.

With respect to the antipathogenic nucleotide sequences, fragments of a nucleotide sequence may encode protein fragments that retain the biological activity of the native proteins, i.e., the sequences set forth in SEQ IDS 1,2, and 3, and hence enhance disease resistance when expressed in a plant. Alternatively, fragments of a coding nucleotide sequence that is useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

A fragment of an antipathogenic nucleotide sequence that encodes a biologically active portion of a protein of the invention will encode at least 15, 25, 30, 40, 50, 75, 100, or 150 contiguous amino acids, or up to the total number of amino acids present in a full-length protein of the invention. Fragments of a nucleotide sequence of the invention that are useful as hybridization probes for PCR primers generally need not encode a biologically active portion of a protein.

A biologically active portion of a protein of the invention can be prepared by isolating a portion of one of the nucleotide sequences of the invention, expressing the encoded portion of the protein (e.g., by recombinant expression in vitro), and assessing the activity of the encoded portion of the protein of interest. Nucleic acid molecules that are fragments of a nucleotide sequence of the invention comprise at least 15, 20, 50, 75, 100, 325, 350, 375, 400, 425, 450, 500, 550, 600, 650, 700, or 800 nucleotides, or up to the number of nucleotides present in a full-length sunflower homologue nucleotide sequence disclosed herein.

By "variants" is intended substantially similar sequences. For nucleotide sequences, conservative variants include those sequences that, because of the degeneracy of the genetic code, encode the amino acid sequence of one of the antipathogenic polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an antipathogenic protein of the invention. Generally, variants-of a particular nucleotide sequence of the invention will have at least 40%, 50%, 60%, 70%, generally at least 75%, 80%, 85%, 87%, preferably about 90%, 91%, 92%, 93%, 94%, 95%, 96%, 97%, and more preferably about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, the defense activation activity as described herein. Such variants may result from, for example, genetic polymorphism or from human manipulation. Biologically active variants of a native antipathogenic protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino-acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the antipathogenic proteins can be prepared by mutations in the DNA. Methods for mutagenesis and nucleotide sequence alterations are well known in the art. See, for example, Kunkel (1985) Proc. Natl. Acad. Sci. USA 82:488–492; Kunkel et al. (1987) Methods in Enzymol. 154:367–382; U.S. Pat. No. 4,873,192; Walker and Gaastra (eds.) Techniques in Molecular Biology, MacMillan Publishing Company, NY (1983) and the references cited therein.

Thus, the promoters and gene nucleotide sequences of the invention include both the naturally occurring sequences as well as mutant forms. Likewise, the proteins of the invention encompass both naturally occurring proteins as well as variations and modified forms thereof. Such variants will continue to possess the desired promoter activity or antipathogenic defense protein activity. Obviously, the mutations that will be made in the DNA encoding a variant protein must not place the sequence out of reading frame and preferably will not create complementary regions that could produce secondary mRNA structure. See, for example, EP Patent Application Publication No. 75,444.

In this manner, the present invention encompasses the antipathogenic proteins as well as components and fragments thereof. That is, it is recognized that component polypeptides or fragments of the proteins may be produced which retain antipathogenic protein activity that enhances disease resistance in a plant. These fragments include truncated sequences, as well as N-terminal, C-terminal, internal and internally deleted amino acid sequences of the proteins.

The deletions, insertions, and substitutions of the protein sequences encompassed herein are not expected to produce radical changes in the characteristics of the antipathogenic proteins. However, when it is difficult to predict the exact effect of the substitution, deletion, or insertion in advance of doing so, one skilled in the art will appreciate that the effect will be evaluated by routine screening assays. That is, the activity of the modified protein sequences can be evaluated by monitoring of the plant defense system. See, for example U.S. Pat. No. 5,614,395, herein incorporated by reference.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire antipathogenic sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the antipathogenic sequences of the invention. Methods for preparation of probes for hybridization and for construction of cDNA and genomic libraries are generally known in the art and are disclosed in Sambrook et al. (1989) Molecular Cloning: A Laboratory Manual (2d ed., Cold Spring Harbor Laboratory Press, Plainview, N.Y.).

For example, the entire antipathogenic sequence disclosed herein, or one or more portions thereof, may be used as a probe capable of specifically hybridizing to corresponding antipathogenic sequence or messenger RNAs. Additionally, the promoter sequences described herein, or one or more portions thereof, may be used a as a probe capable of hybridizing to corresponding promoter sequences.

To achieve specific hybridization under a variety of conditions, such probes include sequences that are unique among antipathogenic sequences or promoter sequence and are preferably at least about 10 nucleotides in length, and most preferably at least about 20 nucleotides in length. Such probes may be used to amplify corresponding antipathogenic sequences or promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C, and a wash in 1×to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37 C, and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (%GC)−0.61 (%form)−500/L; where M is the molarity of monovalent cations, %GC is the percentage of guanosine and cytosine nucleotides in the DNA, % form is the percentage of formamide in the hybridization solution, and L is-the length of the hybrid in base-pairs. The $T_m$ is the temperature (under defined ionic strength and pH) at which 50% of a complementary target sequence hybridizes to a perfectly matched probe. $T_m$ is reduced by about I ° C for each 1% of mismatching; thus, $T_m$,hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$,those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that either have promoter activity or encode for a antipathogenic protein and which hybridize under stringent conditions to the sequences disclosed herein, or to fragments thereof, are encompassed by the present invention. Such sequences will be at least 40% to 50% homologous, about 60% to 70% homologous, and even about 75%, 80%, 85%, 87%, 90%, 91%, 92%, 93%, 94%, 95%, 96%, 97% to 98% homologous or more with the disclosed sequences. That is, the sequence identity of sequences may range, sharing at least 40% to 50%, about 60% to 70%, and even about 75%, 80%, 85%, 87%, 90%, 91%, 92%, 93%, 94%, 95%, 96%, 97% to 98% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (I 981) *Adv. Appl. Math.* 2:482; the homology alignment algorithm of Needleman and Wunsch (1970) *J. Mol Biol.* 48:443–453; the search-for-similarity-method of Pearson and Lipman (1988)

Proc. Natl. Acad. Sci. 85:2444–2448; the algorithm of Karlin and Altschul (1990) Proc. Natl. Acad. Sci. USA 872264, modified as in Karlin and Altschul (1 993) Proc. Natl. Acad. Sci. USA 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237–244 (1988 CABIOS 5:151–153;Corpet et al. (1988) Nucleic Acids Res. 16:10881 -90; Huang et al (1992) CABIOS 8:155–65; and Pearson et al. (1994) Meth. Mol. Biol 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score =100, wordlength =12, to obtain nucleotide sequences homologous to a nucleotide sequence encoding a protein of the invention. BLAST protein searches can be performed with the BLASTX program, score =50, wordlength =3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

For purposes of the present invention, comparison of nucleotide or protein sequences for determination of percent sequence identity to the promoter sequence or the anitpathogenic sequences disclosed herein is preferably made using the Clustal W program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The anti-pathogenic genes and proteins as well as the anti-pathogenic homologue genes and proteins of the invention can also be used to control resistance to pathogens by enhancing the defense mechanisms in a plant. While the exact function of the anti-pathogenic homologues is not known, they are involved in influencing the expression of defense-related proteins. It is recognized that the-present invention is not premised upon any particular mechanism of action of the anti-pathogenic genes. It is sufficient for purposes of the invention that the genes and proteins are involved in the plant defense system and can be used to increase resistance levels in the plant to pathogens.

The plant defense mechanisms described herein may be used alone or in combination with other proteins or agents to protect against plant diseases and pathogens. Other plant defense proteins include those described in copending applications entitled "*Methods for Enhancing Disease Resistance in Plants*", U.S. application Ser. No. 60/076,151, filed Feb. 26, 1998, and U.S. application Ser. No. 60/092,464, filed Jul. 11, 1998, and copending application entitled "Genes for Activation of Plant Pathogen Defense Systems", U.S. application Ser. No. 60/076,083, filed Feb. 26, 1998, all of which are herein incorporated by reference.

The nucleotide sequences of the invention can be introduced into any plant. The genes to be introduced can be conveniently used in expression cassettes for introduction and expression in any plant of interest.

Such expression cassettes will comprise a transcriptional initiation region linked to the nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (I991) *Genes Dev.* 5:141–149; Mogen et al. (1990) *Plant Cell* 2:1261–1272; Munroe et al. (1990) *Gene* 91:151–158; Ballas et al. 1989) *Nuc. Acids Res.* 17:7891–7903; Joshi et al. (1987) *Nuc. Acid Res.* 15:9627–9639.

A number of promoters can be used in the practice of the invention. An inducible promoter can be used to drive the expression of the genes of the invention. The inducible promoter will be expressed in the presence of a pathogen to prevent infection and disease symptoms. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992).*Plant Cell* 4:645–656; and Van Loon (1985) *Plant Mol. Virol.* 4:111–116. See, also the copending applications entitled "Inducible Maize Promoters", U.S. application Ser. No. 60/076,100, filed Feb. 26, 1998 and U.S. application Ser. No. 60/079,648, filed Feb. 27, 1998, and herein incorporated by reference.

Of interest are promoters that are expressed locally at or near the site of pathogen infection. See, for example, Marineau et al. (1987) *Plant Mol. Biol.* 1:335–342; Matton et al. (1989) *Molecular Plant-Microbe Interactions* 2:325–331; Somsisch et al. (1986) *Proc. Natl. Acad. Sci; USA* 83:2427–2430; Somsisch et al. (1988) *Molecular and General Genetics* 2:93–98; and Yang (1996) *Proc. Natl. Acad. Sci. USA* 93:14972–14977. See also, Chen et al. (1996) *Plant J* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound inducible promoter may be used in the constructions of the invention. Such wound inducible promoters include potato proteinase inhibitor (pin II) gene (Ryan et al. *Ann. Rev. Phytopath.* 28:425–449; Duan et al. *Nature Biotechnology* 14:494–498); wun 1 and wun2, U.S. Pat. No. 5,428,148; win 1 and win2 (Stanford et al. *Mol. Gen Genet* 215:200–208); systemin (McGurl et al: *Science* 225:1570–1573); WIP1 (Rohmeier et al. *Plant Mol. Biol.* 22:783–792; Eckelkamp et al. *FEBS Letters* 323:73–76); MPI gene (Corderok et al. *Plant Journal* 6(2):141–150); and the like, herein incorporated by reference.

Constitutive promoters include, for example, the Rsyn7 (copending U.S. application Ser. No. 08/661,601), the scp 1 promoter (copending U.S. application Ser. No. 09/028,819), the ucp promoter, 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. See also, copending application entitled "Constitutive Maize Promoters", U.S. application Ser. No. 60/076,075, filed Feb. 26, 1998, and herein incorporated by reference.

Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant*

*Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505.

The nucleotide sequences for the constitutive promoters disclosed in the present invention, as well as variants and fragments thereof, are useful in the genetic manipulation of any plant when assembled within a DNA construct such that the promoter sequence is operably linked with a heterologous nucleotide sequence whose constitutive expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention are provided in expression cassettes along with heterologous nucleotide sequences for expression in the plant of interest. It is recognized that the promoter sequences of the invention may also be used with their native coding sequences to increase or decrease expression of the native coding sequence, thereby resulting in a change in phenotype in the transformed plant.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389; herein incorporated by reference. Another example is lysine and/or sulfur rich seed protein encoded by the soybean 2S albumin described in U.S. Ser. No. 08/618,91 1, filed Mar. 20, 1996, and the chymotrypsin inhibitor from barley, Williamson et al. (1987) *Eur. J Biochem.* 165:99–106, the disclosures of which are herein incorporated by reference.

Derivatives of the coding sequences can be made by site directed mutagenesis to increase the level of preselected amino acids in the encoded polypeptide. For example, the gene encoding the barley high lysine polypeptide (BHL) is derived from barley chymotrypsin inhibitor, U.S. Ser. No. 08/740,682, filed Nov. 1, 1996, and PCT/US97/20441, filed Oct. 31, 1997, the disclosures of each are incorporated herein by reference. Other proteins include methionine-rich plant proteins such as from sunflower seed (Lilley et al. (1989) Proceedings of the World Congress on Vegetable Protein Utilization in Human Foods and Animal Feedstuffs ed. Applewhite (American Oil Chemists Society, Champaign, Ill.), pp. 497–502; herein incorporated by reference)); corn (Pedersen et al. (1986) *J. Biol. Chem.* 261:6279; Kirihara et al. (1988) *Gene* 71:359; both of which are herein incorporated by reference); and rice (Musumura et al (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example Bacillus thuringiensis toxic protein genes (U.S. Pat. Nos. 5,366,892; 5,747,450; 5,736,514; 5,723,756; 5,593,881; Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. patent application Ser. No. 08/484,815, filed Jun. 7, 1995); avirulence (avr) and disease resistance (R) genes (Jones et al. (1994) *Science* 266:789; Martin et al. (1993) *Science* 262:1432; Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptll gene encodes resistance to the antibiotics kanamycin and geneticin, and the ALS gene encodes resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development. The quality of grain is reflected in traits such as levels and types of oils, saturated and unsaturated, quality and quantity of essential amino acids, and levels of cellulose. In corn, modified hordothionin proteins, described in U.S. Pat. Nos. 5,703,049, 5,885,801, 5,885,802, and 5,990,389, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl- CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eucaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Thus, the heterologous nucleotide sequence operably linked to one of the constitutive promoters disclosed herein may be a structural gene encoding a protein of interest. Examples of such heterologous genes include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. More particularly, the constitutive promoters disclosed herein and identified as weak constitutive promoters are useful in transforming plants to constitutively express an avirulence gene as disclosed in the copending applications both entitled "Methods for Enhancing Disease Resistance in Plants," U.S. application Ser. No. 60/075,151, filed Feb. 26, 1998, and U.S. application Ser. No. 60/092,464, filed Jul. 11, 1998, both of which are herein incorporated by reference. Such weak promoters may cause activation of the plant defense system short of hypersensitive cell death. Thus, there is an activation of the plant defense system at levels sufficient to protect from pathogen invasion. In this state, there is at least a partial activation of the plant defense system wherein the plant produces increased levels of antipathogenic factors such as PR proteins, i.e., PR-1, cattiness, a-glucanases, etc.; secondary metabolites; phytoalexins; reactive oxygen species; and the like.

Alternatively, the heterologous nucleotide sequence operably linked to one of the constitutive promoters disclosed herein may be an antisense sequence for a targeted gene. By "antisense DNA nucleotide sequence" is intended a sequence that is in inverse orientation to the 5' to 3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequences disclosed herein may be operably linked to antisense DNA sequences to reduce or inhibit expression of a native protein in the plant.

The genes and promoters of the invention-are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray et al. (1989) *Nuc. Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader. (Maize Dwarf Mosaic Virus); *Virology* 154:9–20), and human immunoglobulin heavy-chain binding protein (BiP), (Macejak et al. (1991) *Nature* 353:90–94; untranslated leader from the coat protein mRNA of alfalfa mosaic virus (AMV RNA 4), (Jobling et al. (1987) *Nature* 325:622–625; tobacco mosaic virus leader (TMV), (Gallie, D. R. (1989) *Molecular Biology of RNA* 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The genes of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl Acad. Sci. USA* 83:5602–5606, Agrobacterium mediated transformation (Hinchee et al. (1988) Biotechnology 6:915–921), direct gene transfer (Paszkowski et al. (1984) *EMBO J.* 3:2717–2722), and ballistic particle acceleration (see, for example, Sanford et al., U.S. Pat. No. 4,945,050; Tomes et al. Direct DNA Transfer into Intact Plant Cells via Microprojectile Bombardment; In Gamborg and Phillips (Eds.) *Plant Cell, Tissue and Organ Culture: Fundamental Methods*, Springer-Verlag, Berlin (1995); and McCabe et al. (1988) Biotechnology 6:923–926). Also see, Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674(soybean); McCabe et al. (1988) *Bio/Technology* 6:923–926 (soybean); Datta et al. (1990) Biotechnology 8:736–740 (rice); Klein et al. (1988) Proc. *Natl. Acad. Sci. USA* 5:4305–4309 (maize); Klein et al. (1 988) *Biotechnology* 6:559–563 (maize); Tomes et al. Direct DNA Transfer into Intact Plant Cells via Microprojectile Bombardment; In Gamborg and Phillips (eds.) *Plant Cell, Tissue and Organ Culture: Fundamental Methods*, Springer-Verlag, Berlin (1995) (maize); Klein et al. (1988) *Plant Physiol.* 91:440–444(maize); Fromm et al. (I990) Biotechnology 8:833–839 (maize); Hooydaas-Van Slogteren et al. (1984) *Nature (London)* 311:763–764; Bytebier et al. (1987) *Proc. NatL. Acad. Sci. USA* 84:5345–5349 (Liliaceae); De Wet et al. (1985) In The Experimental Manipulation of Ovule Tissues ed. G. P. Chapman et al., pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of botany* 75:407–413 (rice); Osjoda et al. (1996) *Nature Biotechnology* 14:745–750 (maize via Agrobacterium tumefaciens); all of which are herein incorporated by reference.

The cells, which have been transformed, may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The methods of the invention can be used with other methods available in the art for enhancing disease resistance in plants.

Methods for increasing pathogen resistance in a plant are provided. The methods involve stably transforming a plant with a DNA construct comprising an anti-pathogenic nucleotide sequence of the invention operably linked to promoter that drives expression in a plant. Such methods find use in agriculture particularly in limiting the impact of plant pathogens on crop plants. The anti-pathogenic nucleotide sequences comprise sunflower genes. Particularly, the sunflower genes are selected from the genes encoding PR5, defensin and BBE. While the choice of promoter will depend on the desired timing and location of expression of the anti-pathogenic nucleotide sequences, preferred promoters include constitutive and pathogen-inducible promoters.

Methods are provided for increasing the resistance of a plant to a pathogen involving stably transforming a plant with a DNA construct comprising a nucleotide sequence of an inducible promoter of an antipathogenic gene of the invention operably linked to a second nucleotide sequence. Preferably, the promoter is selected from the promoters of genes encoding a PR5, a BBE homologue or a defensin. More preferably, the promoter has a nucleotide sequence selected from the sequences set forth in SEQ ID:7, SEQ ID:8, and SEQ ID:9. Although any one of a variety of second nucleotide sequences may be utilized, preferred embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome.

Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Examples of such second nucleotide sequences include, but are not limited to, sequences encoding PR1, different members of defensin, or BBE, PR5, antifungal peptides such as tachyplesin, chitinases, glucanase, etc.

Additionally provided are transformed plants, plant cells, plant tissues and seeds thereof.

By "pathogenic agent" are intended pathogenic organisms such as fungi, bacteria, viruses, and disease causing microorganisms. Additionally included are nematodes, insects and the like. Pathogens of the invention include, but are not limited to, viruses or viroids, bacteria, insects, nematodes, fungi, and the like. Viruses include tobacco or cucumber mosaic virus, ringspot virus, necrosis virus, maize dwarf mosaic virus, etc.

Specific fungal and viral pathogens for the major crops include: Soybeans: *Phytophthora megasperma* fsp. glycinea, *Macrophomina phaseolina, Rhizoctonia solani, Scierotinia sclerotiorum, Fusarium oxysporum, Diaporthe phaseolorum* var. *sojae (Phomopsis sojae), Diaporthe phaseolorunm* var. *caulivora, Sclerotium roistii, Cercospora kikuchii, Cercospora sojina, Peronospora manshurica, Colletotrichum dematium (Colletotichum truncatum), Corynespora cassiicola, Septoria glycines, Phyllosticta sojicola, Alternaria altenzata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythiuin aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alterniata*; Alfalfa: *Clavibater michiganese subsp. insidiosum, Pythium ultimum, Pythium irregulare, Pythium splendens, Pythium debarjanum, Pythium aphanidermatum, Phytophthora megasperma, Peronospora trifoliorum, Phoma medicaginis* var. *medicaginis Cercospora medicaginis, Pseudopeziza medicaginis, Leptotrochila medicaginis, Fusar-atrum, Xanthomonas campestris* p.v. *alfalfae, Aphanomyces euteiches, Stemphylium herbarum, Stemphyliurm alfalfae*; Wheat: *Pseudomonas syringae* p.v. *atrofaciens, Urocystis. agropyri, Xanthomonas campestris* p.v. *translucens, Pseudomonas syringae* p.v. *syringae, Alternaria alternata, Cladosporium herbatnum, Fusarium gramiinearum, Fusarium avenaceum, Fusarium culmorum, Ustilago tritici, Ascoclyta tritici, Cephalosporium gramineum, Collotetrichumn graminicola, Erysiphe graminis* f.sp. *tritici, Puccinia gramnin is* f.sp. *tritici, Puccinia recondita* f.sp. *tritici, Puccinia striiformis, Pyreno-*

*phora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiortiun,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearim, Rhizopus oryzae, Rhizopus arrhizus, Rhizopus stolonifer, Puccinia helianthi, Verticillium clahliae, Erwinia carotovorum* pv. *carotovora, Cephalosporium acremonium, Phytophthora cryptogea, Aibugo tragopogonis, Orobanche cumana;* Corn: *Fusarium moniliforme* var. *subglutinans, Erwinia stewartii, Fusarium moniliforme, Gibberella zeae (Fusarium gramiinearum), Stenocarpella maydi (Diplodia maydis), Pythium irregulare, Pythiumn debaryanum, Pythium graminicola, Pythium splendens, Pythiumn ultimum, Pythium aphanidermatum, Aspergillusflavus, Bipolaris maydis* O, T(*Cochliobolus heterostrophus*), *Helminthosporium carbonum* I, II & III (*Cochliobolus carbonum*), *Exserohilum turcicum* I, II & III, *Helminthosporium pedicellatum, Physodermia maydis, Phyllosticta maydis, Kabatie-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chr, Zscanthemi* pv. *zea, Erwinia corotovora, Corrnstunt spiroplasma, Diplodia macrospora, Sclerophthora miacrospora, Peronosclerospora sorghi, Peronosclerospora philippinensis, Peronosclerospora maydis, Peronosclerospora sacchari, Spacelotheca reiliana, Physopella zeae, Cephalosporiumn maydis, Caphalosporiumn acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilumn turcicum, Colletotrichurn graminicola (Glomerella graminicola), Cercospora sorghi, Gloeocercospora sorghi, Ascochyta sorghina, Pseudornonas syringae* p.v. *syringae, Xanthomonas camnpestris* p.v. *holcicola, Pseuclomonas andropogonis, Puccinia purpurea, Macrophomina phaseolina, Perconia circinata, Fusariumn imoniliforniie, Alternaria alternate, Bipolaris sorghicola, Helminthosporiurm sorghicola, Curvularia lunata, Phoma insidiosa, Pseudomonas avenae (Pseudornonas alboprecipitans), Ramulispora sorghi, Ramnulispora sorghicola, Phyllachara sacchari, Sporisoriumn reilianum (Sphacelotheca reiliana), Sphacelotheca crienta, Sporisoriumn sorghi,* Sugarcane mosaic H, Maize Dwarf Mosaic Virus A & B, *Claviceps sorghi, Rhizoctonia solani, Acremoniurm stricturn, Sclerophthona macrospora, Peronosclerospora sorghi, Peronosclerospora philippinensis, Sclerospora graminicola, Fusariurm graminearurm, Fusarium ovysporum, Pythium arrhenlomanes, Pythiurm graminicola,* etc.

Nematodes include parasitic nematodes such as root knot, cyst, reniform and lesion nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; *Melanotus* spp., wireworms; *Cyclocephala borealis,* northern masked chafer (white grub); *Cyclocephala immaculata,* southern masked chafer (white grub); *Popillia japonica,* Japanese beetle; *Chaetocniema pulicaria,* corn flea beetle; *Sphenophorus maidis,* maize billbug; *Rhopalosiphuni maidis,* corn leaf aphid; *Anuraphis maidiradicis,* corn root aphid; *Blissus leucopterus leucopterus,* chinch bug; *Melanoplus femurnibrum,* redlegged grasshopper; *Melanoplus sanguinipes,* migratory grasshopper; *Hylemya platura,* seedcorn maggot; *Agromiyza parvicornis,* corn blot leafminer; *Anaphothrips obscrurus,* grass thrips; *Solenopsis milesta,* thief ant; *Tetranychus urticae,* two spotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; *Eleodes, Conoderus,* and *Aeolis* spp., wireworms; *Oulema melanopus,* cereal leaf beetle; *Chaetocnema pulicaria,* corn flea beetle; *Sphenophorus maidis,* maize billbug; *Rhopalosiphum miaiclis;* corn leaf aphid; *Sipha flava,* yellow sugarcane aphid; *Blisstus leucopterus leucopterus,* chinch bug; *Contarinia sorghicola,* sorghum midge; *Tetranychus cinnabarinus,* carmine spider mite; *Tetranychus urticae,* two spotted spider mite; Wheat: *Pseudaletia uniipunctata,* army worm; *Spodoptera frugiperda,* fall arnyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera pundcata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femnurrubrum,* redlegged grasshopper; *Melanoplus differentialis,* differential grasshopper; *Melanoplis sanguinipes,* migratory grasshopper; *Mayetiola destructor,* Hessian fly; *Sitodiplosis mosellana,* wheat midge; *Meromyza americana,* wheat stem maggot; *Hylemrya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Botlhyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonornus grandis,* boll weevil; *Aphis gossypli,* cotton aphid; *Pseudatomoscelis seriatus,* cotton flea hopper; *Trialeuroles abutilonea,* bandedwinged whitefly; *Lygus lineolaris,* tarnished plant bug; *Melanoplus femurrubrumn,* redlegged grasshopper; *Melanoplus differentialis,* differential grasshopper; *Thrips tabaci,* onion thrips; *Franklinkiella fusca,* tobacco thrips; *Tetranychus*

*cinnabarinus*, carmine spider mite; *Tetranychus urticae*, two spotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophiliis*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachtia varivestis*, Mexican bean beetle; *Myzus persicae*, green peach aphid; *Enipoasca fabae*, potato leafhopper; *Acrosternum hilare*, green stink bug; *Melanoplus femrurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two spotted spider mite; Barley: *Ostrinia nubilalis*, European corn borer; *Agrotis ipsilon*, black cutworm; *Schizaphis graminumn*, greenbug; *Blissus leucopterus leucopterus*, chinch bug; *Acrosternurm hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamnestra configurata*, Bertha armyworm; *Plutella xylostella*, Diamond-back moth; Delia ssp., Root maggots.

The present invention also provides isolated nucleic acids comprising polynucleotides of sufficient length and complementarity to a gene of the invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of polypeptides, or for use as immunogens in the preparation and/or screening of antibodies. The isolated nucleic acids of the present invention can also be employed for use in sense or antisense suppression of one or more genes of the invention in a host cell, tissue, or plant. Attachment of chemical agents, which-bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated genes of the invention from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes,* 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention provides a method of genotyping a plant comprising a polynucleotide of the present invention. The plant may be a monocot, such as maize or sorghum, or alternatively, a dicot, such as sunflower or soybean. Genotyping provides a means of distinguishing homologues of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Texas, pp. 7–21.

The particular method of genotyping in the present invention may employ any number of molecular marker analytic techniques such as, but not limited to, restriction fragment length polymorphisms (RFLPs). Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the invention.

In the present invention, the nucleic acid probes employed for molecular marker mapping of plant.nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

Methods are provided for controlling plant pathogens comprising applying an anti-pathogenic amount of a protein or composition of the invention to the environment of the pathogens. By "controlling plant pathogens" is intended killing the pathogen or preventing or limiting disease formation on a plant. By "anti-pathogenic amount" is intended an amount of a protein or composition that controls a pathogen. The proteins and compositions can be, applied to the environment of the pathogen by methods known to those of ordinary skill in the art.

The proteins of the invention can be formulated with an acceptable carrier into a pesticidal composition(s) that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a U.V. protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The active ingredients of the present invention are normally applied in the form of compositions and can be applied to the crop area or plant to be treated, simultaneously or in succession, with other compounds. Preferred methods of applying an active ingredient of the present invention or an agrochemical composition of the present invention, which contains at least one of the proteins of the present invention, are foliar application, seed coating and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g. butyl-naphthalene sulfonate; salts of sulfonated naphthalene-forrnaldehyde condensates; salts of sulfonated phenol-formaldehyde condensates; more complex sulfonates such as the amide sulfonates, e.g. the sulfonated condensation product of oleic acid and N-methyl taurine; or the dialkyl sulfosuccinates, e.g. the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4, 7-diol, or ethoxylated acetylenic glycols. Examples of a cationic surface-active agent include, for instance, an aliphatic mono-, di, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions-will be administered at the labeled rate for the commercial product, preferably about 0.01 lb–5.0 lb. per acre when in dry form and at about 0.01 pts.–10 pts. per acre when in liquid form.

In a further embodiment, the compositions, as well as the proteins of the present invention can be treated prior to formulation to prolong the activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason, Animal Tissue Techniques, W.H. Freeman and Co., 1967).

The compositions can be applied to the environment of a pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. It is generally important to obtain good control of pests in the early stages of plant growth, as this' is the time when the plant can be most severely damaged. The compositions of the invention can conveniently contain another insecticide or pesticide if this is thought necessary.

Plants to be protected within the scope of the present invention include but are not limited to cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, peanuts, lentils, peas, soybeans), oil plants (rape, mustard, poppy, olives, safflowers, sunflowers, coconuts, castor oil plants, cocoa beans, oil palms), cucumber plants (cucumber, marrows, melons), fiber plants (cotton, flax, hemp, jute), citrus fruit (oranges, lemons, limes, grapefruit, mandarins), vegetables (spinach, lettuce, asparagus, cabbages and other Brassicae, carrots, onions, tomatoes, potatoes, paprika), lauraceae (avocados, cinnamon, camphor), deciduous trees and conifers (e.g. linden-trees, yew-trees, oak-trees, alders, poplars, birchtrees, firs, larches, pines), or plants such as maize, turf plants, tobacco, nuts, coffee, sugar cane, tea, hops, bananas and natural rubber plants, as well as ornamentals.

In a further embodiment, formulations of the present invention for use as antimicrobial therapies comprise the anti-pathogenic proteins in a physiologically or pharmaceutically acceptable carrier, such as an aqueous carrier. Thus, formulations for use in the present invention include, but are not limited to, those suitable for parenteral administration, including subcutaneous, intraderinal, intramuscular, intravenous and intraarterial administration, as well as topical administration: The formulations may conveniently be presented in unit dosage form and may be prepared by any of the methods well-known in the art. Such formulations are described in, for example, *Remington's Pharmaceutical Sciences* 19th ed., Osol, A. (ed.), Mack Easton Pa. (1980).

In the manufacture of a medicament according to the invention, the anti-pathogenic compositions are typically admixed with, inter alia, an acceptable carrier. The carrier must, of course, be acceptable in the sense of being compatible with any other ingredients in the formulation and must not be deleterious or harmful to the patient. The carrier may be a solid or a liquid. One or more anti-pathogenic proteins may be incorporated in the formulations of the invention, which may be prepared by any of the well-known techniques of pharmacy consisting essentially of admixing the components, optionally including one or more accessory therapeutic ingredients.

Formulations of the present invention may comprise sterile aqueous and non- aqueous injection solutions of the active compound, which preparations are preferably isotonic with the blood of intended recipient and essentially pyrogen free. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation the anti-pathogenic protein may be contained within a lipid particle or vesicle, such as a liposome or microcrystal, which may be suitable for parenteral administration. The particles may be of any suitable structure, such as unilamellar or plurilamellar, so long as the targeted cassette is contained therein. Positively charged lipids such as N-[ 1 -(2,3-dioleoyloxi)propyl]-N,N, N-trimethyl-amoniummethylsulfate, or "DOTAP", are particularly preferred for such particles and vesicles. The preparation of such lipid particles is well-known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The dosage of the anti-pathogenic protein administered will vary with the particular method of administration, the condition of the subject, the weight, age, and sex of the subject, the particular formulation, the route of administration, etc. In general, the protein will be administered in a range of about 1 $\mu$g/L to about 10 $\mu$g/L.

The following examples are offered by way of illustration and not by way of limitation.

EXPERIMENTAL

Materials and Methods

Plant Material

Sunflower plants were grown in the greenhouse and growth chamber. The sunflower line SMF 3 and oxox-transgenic sunflower (line 193870 and 610255) were used for RNA profiling study by CuraGen using methods described in U.S. Pat. No. 5,871,697 to Rothberg et al., and U.S. Pat. No. 5,972,693 to Rothberg et al., both incorporated herein by reference. Sunflower pathogen, Sclerotinia sclerotiorum was maintained on plate at 20° C. in dark.

Preparation of total RNAs for RNA profiling study and Northern analysis

Plant materials were ground in liquid nitrogen, and total RNA was extracted by the Tri-Reagent Method (Sigma). For each RNA profiling study, RNA samples from 6-week-old sunflower leaves and stems of transgenic sunflower plants expressing a wheat oxalate oxidase gene were compared with those from sunflower line SMF3. Total RNA (20 $\mu$g) was separated in a 1% agarose gel containing formaldehye. Ethidium bromide was included to verify equal loading of RNA. After transfer onto Hybond N+ membrane (Amersham), the blots were hybridized with $^{32}$P-labelled PR5, defensin or BBE cDNA probes. A duplicate blot was hybridized with an 1 8S rRNA probe as a control. Hybridization and washing conditions were performed according to Church et al. (1984) *Proc. Natl. Acad. Sci. USA* 81:1991–1995.

RNA Profiling Technology

Total RNA was analyzed using the gene expression profiling process (GeneCalling®) as described in U.S. Pat. No. 5,871,697, herein incorporated by reference. A number of distinct transcripts increased in abundance following the oxidative burst and cDNAs corresponding to a portion of these transcripts were cloned and sequenced.

Isolation of full-length or flanking sequences by PCR amplification of cDNA ends Three defense-related cDNAs were isolated by using RNA profiling and PCR-based technologies. RNA profiling studies were conducted through the collaboration with CuraGen Corporation. FIG. 1 illustrates the cloning strategy used. The sequence information generated was used for designing gene-specific primers to amplify both 3'and/or 5' end regions of the target genes using the PCR-based, RACE method. Sclerotinia-infected and oxox-induced cDNA libraries or cDNAs made using a Marathon cDNA Amplification Kit (Clontech) were utilized as a source of templates for PCR amplification. To facilitate cloning full-length cDNAs from the initially cloned regions, we designed a pair of 28 bp vector primers flanking cDNAs on the both ends (3' and 5') of the pBS vector and directionally amplified either the 5' or 3' end of a cDNA with one of vector primers (pBS-upper or pBS-lower) and a gene-specific primer. Once the anticipated 5' end of a specific gene with an intact ATG start codon was cloned and sequenced, the full-length cDNA was amplified using a second gene-specific primer containing corresponding to sequence upstream of the ATG and a vector primer at 3' end. The PCR products were cloned and sequenced by standard methods. PCR reactions were performed in a total volume of 25 $\mu$l in 10 mM Tris-HCl, pH 8.3; 1.5 mM $MgCl_2$; 50 mM KCl; 0.1 mM dNTPs; 0.25 $\mu$M of each primer with 0.5 units of advantage cDNA polymerase mix (Clontech) or Pwo DNA polymerase (Boehringer). Genomic DNA and/or cDNA library mixtures were used as a source of templates for PCR amplification.

Isolation of Pathogen-inducible Promoters

Promoter regions of PR5, defensin, and BBE were isolated from sunflower genomic DNA using Universal GenomeWalker Kit (Clontech) according to the manufacturer's instructions. Restriction digested genomic DNAs were ligated with an adapter to construct pools of genomic DNA fragments for walking by PCR (Siebert et al. (1995) *Nuc. Acids Res.* 23:1087–1088).

Analysis of Amplified PCR Products

Amplified PCR fragments with the expected sizes were individually sliced out of a gel for a second round of PCR amplification with the same conditions as the initial PCR. Each second-round PCR product yielding a single band of the expected size was cloned into a TA vector (Clontech) according to the manufacturer's instructions. Identified positive clones were selected for DNA sequencing using an Applied BioSystems 373A (ABI) automated sequencer at the Nucleic Acid Analysis Facility of Pioneer Hi-Bred International, Incorporated. DNA sequence analysis was carried out with the Sequencer (3.0). Multiple-sequence alignments (Clustal W) of the DNA sequence were analyzed with the Curatool (CuraGen).

Construction of the Sclerotinia-infected and Resistance-enhanced (Oxox-induced) Sunflower cDNA Libraries Six-week-old SMF3 sunflower plants were infected with Sclerotinia sclerotrium by petiole inoculation with Sclerotinia-infested carrot plugs. Six days after infection, leaf and stem tissues were collected from infected plants for total RNA isolation. Total RNA was also isolated from sunflower oxox-transgenic plants (line 610255) expressing a wheat oxalate oxidase gene at the six-week stage. Previous studies have shown that elevated levels of $H_2O_2$, SA, and PR1 protein were deducted in oxox-transgenic plants at six-week stage and the plants showed more resistance to Sclerotinia infection (WO 99/04013). The mRNAs were isolated using an mRNA purification kit (BRL) according to manufacturer's instruction. cDNA libraries were constructed with the ZAP-cDNA synthesis kit into pBluescrip phagemid (Stratagene). A cDNA library mixture for PCR cloning was made of oxox transgenic stem and Sclerotinia-infected leaf libraries (1:2 mix).

Fungal Infection and Chemical Treatments

Sunflower plants SMF3 were planted in 4-inch pots and grown in the greenhouse for four weeks. After transfer to the growth chamber, plants were maintained under 12 hour photoperiod at 22° C. with a 80% relative humidity. Six-week-old plants were inoculated with Sclerotinia-infested carrot plugs or sprayed with one of four different chemical treatments. For each plant, three petioles were inoculated and wrapped with 1×2 inch parafilm. Plant tissue samples were collected at different time points by immediately freezing in liquid nitrogen and then stored at −80° C.

Results

RNA Profiling Study of Oxox-transgenic Sunflower Plants

Resistance to the fungal pathogen Sclerotinia is a trait of major importance for crops such as sunflower, canola, and soybean. Sunflower Sclerotinia disease can be established at various developmental stages with the main targets being head, stem, and root tissues. This suggests that resistance genes need to be constitutively expressed in multiple tissues. The major toxic and pathogenic factor produced by Sclerotinia is oxalic acid that can be converted into $H_2O_2$ and $CO_2$ by oxalate oxidase. A candidate gene for detoxifying oxalate is the wheat oxalate oxidase (oxox) which have been used to transform a sunflower inbred line. Expression of oxox by a constitutive promoter significantly enhances resistance to Sclerotinia in sunflower. In a growth chamber experiment, lesion size was six-fold lower in oxox-transgenic sunflower plants upon infection with Sclerotinia mycelia relative to untransformed plants. At the six-week-old stage, the oxox-transgenic sunflower plants displayed a lesion mimic in the mature leaves. The enhanced Sclerotinia resistance of sunflower oxox transgenics is closely related to the observed elevated levels of SA and PR proteins (WO 99/04013).

In the RNA profiling analysis, 30 bands were induced and 30 bands were repressed in the oxox-transgenic stem and leaf tissues compared to non-transformed SMF3 plants. Three of the induced bands were sequenced (Table 1), and the sequence information was used to clone the full-length clones.

Cloning of Full-length cDNAs Related to Sunflower Disease Resistance

A PCR-based cloning method was developed to efficiently isolate full-length cDNAs of the plant defense genes, from sunflower cDNA libraries (FIG. 2). A cDNA library mixture containing both oxox-transgenic cDNA library and Sclerotinia-infected cDNA library (1:2 mix) was used as template for PCR amplification. Using cDNA libraries as DNA template in PCR amplification had two benefits: (1) the number of unexpected PCR products was reduced as compared to genomic DNA as a source of template, and (2) disease-induced cDNA libraries increased the chance of isolating defense-related genes. To facilitate cloning full-length cDNAs from the initial cloned regions, we designed a pair of 28 bp vector primers (Table 1) flanking cDNAs on the both ends (3' and 5') of the vector and directionally amplified either the 5' or 3' end of a cDNA with one vector primer and a gene-specific primer (FIG. 1 and Table 1). The anticipated 5' end of specific gene with the intact ATG-start codon was cloned and sequenced. The full-length cDNA was amplified using a second gene-specific primer containing sequence upstream of the ATG and a vector primer at the 3' end. The PCR products were cloned and submitted to sequence analysis.

Table 1 provides RNA profiling band sequences (PBS) and oligonucleotide sequences used for PCR amplification of the cDNAs and promoter regions. Oligonucleotide PBS-upper (P3) and PBS-lower (P4) were two primers located at the ends of cDNA library vector, as indicated in FIG. 2. For each targeted gene, two or three gene-specific primers were made to complete the 5'-end RACE (PI), the 3'-end RACE (P2), and the full-length RACE (P5). The additional antisense primers were made for cloning promoter regions of PR5, defensin, and BBE, using the GenomeWalker kit (Clontech) (Band h0a0-231.3, PR5; band d010-113.9, defensin; and n0s0-162.7, BBE).

TABLE 1

Oligonucleotide sequences used for PCR amplification of cDNAs and promoter regions:

cDNA cloning:
Library vector (pBS):
PBS-upper:  GCGATTAAGTTGGGTAACGCCAGGGT (SEQ ID NO:26)
PBS-lower:  TCCGGCTCGTATGTTGTGTGGAATTG (SEQ ID NO:27)
PR5:        TGATCAGTTTTGTACACGGTGCAAGGGTTATTGCACCCGCCAGAGCCC TABLE 1-continued Oligonucleotide sequences used for PCR amplification of cDNAs and promoter regions:

| | |
|---|---|
| h0a0-231.3: | GTAACTCNCCAGGACACTGGCCATTGATATCCGCAGTACATGAGATAC CCCGGGTGCACCCATTAGAATTGGGTCTAAACACCATCGGCACATTGA ATCCGTCCACAAGAGAAATGTCAAAGAAATCAAGATTGTTGAACTGGT TCCAAGCGTACTCGGCCCATGTGTTTGGGTGGGGTACC (SEQ ID NO:28) |
| Sense: | CCGAGTACGCTTTAACCAGT (SEQ ID NO:29) |
| Antisense: | TCCGCAGTACATGAGATACCC (SEQ ID NO:30) |
| Full-RACE: (P5) | ACAATGACAACCTCCACCCTTCCCACTTT (SEQ ID NO:31) |
| Definsin: d010-113.9: | TCCGGACCATGTCTGGCTTGCCTTCTCACATAATTCTCCTTTCACCGAT CCGATTTCTGAGATAGCAAGAACAAAGAGAAGCAGAAGAAAAGCATT GAAAGCAACTGAAATT (SEQ ID NO:32) |
| A-sense: | GACCATGTCTGGCTTGCCTTCTCACA (SEQ ID NO:33) |
| full-RACE: (P5) | GAGCTTGAGCTTAGTTCAGTAACTTAAAAATGGCC (SEQ ID NO:34) |
| BBE: n0s0-162.7: | TGTACACATTTGGTGGGAAGATGGAGGAGTACTCAGATACAGCAATTC CGTATCCCCATAGAGCTGGGGTGTTGTACCAAGTGTTCAAGAGGGTGG ACTTCGTGGATCAGCCTTCGGACAAGACCTTGATATCACTCAGACGGT TGGCTTGGCTCCGAAGCTT (SEQ ID NO:35) |
| Sense: | CCAACCGTCTGAGTGATATCAAGG (SEQ ID NO:36) |
| A-sense: | GGGAAGATGGAGGAGTACTCAGAT (SEQ ID NO:37) |
| Full-RACE: (P5) | CGGCACGAGTAACTCTCGTTCAGTGTTCC (SEQ ID NO:38) |
| Promoter cloning: | |
| AP Primer: | GTAATACGACTCACTATAGGGC (SEQ ID NO:39) |
| PR5 A-sense2: | CGAATAGTGAACACGGCTGCATTGGT (SEQ ID NO:40) |
| BBE A-sense2: | GCTGCAGCTTGCCAAATGGGTATGTA (SEQ ID NO:41) |

*Oligonucleotide PBS-upper (P3) and PBS-lower (P4) were two primers located at the ends of cDNA library vector, as indicated in FIG. 2. For each targeted gene, two or three gene specific primers were made to complete the 5' end RACE (P1), the 3' end RACE (P2), and the full-length RACE (P5). The additional antisense primers were made for cloning promoter regions of PR5-1 and BBE, using the genome walker kit from Clontech. Band h0a0-231.3, PR5-1; band d010-113.9, defensin; and n0s0-162.7, BBE.

Cloning Sunflower PR5–1 cDNA and its Promoter

A full-length cDNA encoding pathogenesis-related protein-5 (PR5-1) was isolated from sunflower. The nucleotide sequence of PR5-1 is set forth in SEQ ID:4 and the amino acid sequence encoded by this nucleotide sequence is set forth in SEQ ID: 1. The sunflower PR5-1 protein with its amino-terminal signal sequence is 222 amino acids in length with a calculated molecular mass of 25 kDa and a pI of 6.71. Database searches with predicted amino acid sequence revealed significant sequence similarity with previously reported PR5 proteins from other plant species. The 5'-flanking sequence of the PR5-1 gene contains two potential pathogen-responsive MRE-like elements. These elements have the sequences TGTAGG (nucleotides 23–28, SEQ ID:7) and AACAAAA (nucleotides 247–253, SEQ ID:7). The PR5-1 promoter region also contains a CAAT box (nucleotides 438–441, SEQ ID:7) and a TATA box (nucleotides 485–490, SEQ ID:7). FIG. 2 shows the alignment of amino acid sequence of PR5-1 from sunflower with other PR5 or osmotin-like proteins from grape, soybean, tomato, and potato. Sunflower PR5-1 shows the highest sequence similarity to P21 protein (78% amino acid identity; 80% similarity) from soybean (Swiss-Prot P205096) followed by the osmotin-like protein from grape (Swiss-Prot 004708 ; 72% amino acid identity; 77% similarity), where sequence comparisons were performed with the GAP algorithm described above using default parameters.

Berberine Bridge Enzyme (BBE) cDNA and its Promoter

A full-length cDNA encoding a BBE homologue was isolated from sunflower. The full-length cDNA set forth in SEQ ID:5 is 1809 nucleotides long with an open reading frame encoding a protein-of 542 amino acids (SEQ ID:2) and a calculated molecular mass at 61.41 kDa and a pI of 8.18 (FIG. 5). The BBE promoter region, contains a potential MRE-like element with the sequence TGTAGG (nucleotides, 139–144, SEQ ID:8). The BBE promoter also contains a CAAT box (nucleotides 278–281, SEQ ID:8), and a TATA box (nucleotides 299–304, SEQ ID:8). The isolated cDNA shares homology with BBE cDNAs from California poppy and opium poppy (FIG. 3) and two published sunflower cDNAs encoding carbohydrate oxidases (WO 98/13478), which have antifungal activity, specifically against *Phytophthora* and *Pythium* species (FIG. 3). The amino acid sequence alignment indicates 42% identity and 52% similarity between the sunflower BBE and the previously patented sequences (Sunflower-15 and Sunflower-17 from WO 98/13478), where the comparison was performed with the GAP algorithm described above using the default parameters.

Inducible Sunflower Defensin cDNA and its Promoter

The sunflower defensin cDNA is 556 nucleotides long with an open reading frame starting at nucleotide 36 and ending at nucleotide position 362 (SEQ ID:6). The deduced polypeptide is 108 amino acids long and contains a putative signal peptide at the amino-terminal end (SEQ ID:3). The cloned defensin promoter contains two W-boxes with the nucleotide sequence TTGACC (nucleotides 221–226, and nucleotides 1075–1080, SEQ ID:9), and a G-box with sequence CACGTG (nucleotides 564–569, SEQ ID:9). These cis-elements are potentially related to plant defense response. The defensin promoter also contains a TATA box (nucleotides 857–860, SEQ ID:9).The protein has significant homology to other reported plant defensins (FIG. 4). Eight important cysteine residues in this novel defensin were highly conserved among all other known plant defensins.

Accumulation of PR5–1, Defensin and BBE Transcripts in Response to Fungal Pathogen Infection and Chemical Treatments The expression of many of PR5 and defensin genes were induced by biotic and abiotic stresses (Terra et al. (1988) Planta 206:117–124); Ward et al. (1991) Plant Cell 3:1085–1094). Oxalic acid (OA), a compound produced by Sclerotinia and many other fungal pathogens in planta, plays an important role in the disease infection process (Noyes et al. (1981) Physiol. Plant Path. 18:123–132). Salicylic acid, jasmonic acid and $H_2O_2$ have been implicated as having a central role in plant disease resistance and systemic acquired resistance, and have been shown to induce the accumulation of many PR proteins, including PR5 protein and defensin in Arabiclopsis (Blechert et al. (1995) Proc. Natl. Acad. Sci. USA 92:4099–4105; Terra et al. (1988) Planta 206:117–124; Noyes et al. (1981) Phiysiol. Plant Path. 18:123–132).

Six-week-old sunflower plants were either inoculated with Sclerotinia or treated with different chemicals. Plants inoculated with Sclerotinia showed wilt symptoms on inoculated leaves 24 hours after inoculation and lesions started to spread to the main stem 3 days after infection. For the infection experiment, plant tissues were collected at 0, 6, 12, 24 hours, and 3, 6 and 10 days after infection. Chemical-treated plants were collected at 0, 6, 12, and 24 hours after foliar application.

Northern blot analysis revealed that sunflower PR5-1 protein was induced in leaf and stem tissues of the Sclerotittia-infected and oxox transgenic plants. RNA profiling indicated that PR5-1 transcript level in the oxox transgenic plants was 9-fold higher than in the untransformed line (SMF3). Northern results indicated that the sunflower PR5-1 was up-regulated significantly by Jasmonic acid (45 µM) and oxalic acid (5 mM). Up regulation was less pronounced between control and salicylic acid, and $H_2O_2$ treated samples.

BBE transcripts were highly induced in oxox-transgenic and Sclerotinia infected sunflower leaves. However, BBE transcripts were not detected in either control or infected stem samples. Northern blot analysis confirmed the RNA profiling result of increased BBE transcripts in oxox transgenic plants. The chemical induction experiment revealed that BBE expression was induced by oxalic acid, $H_2O_2$, SA and JA at early time points and returned to the normal level within 24 hours after application.

The expression of the isolated sunflower defensin gene appeared to be different from other defensin genes. In general, plant defensin genes such as Arabidopsis PDF1.2 and radish defensin are induced by pathogens via an SA-independent and JA-dependent pathway. Northern results indicated that the sunflower defensin was up-regulated significantly by salicylic acid (5 mM), oxalic acid (5 mM) and $H_2O_2$ (5 mM). However, there was little difference between control and Jasmonic acid treated samples.

Defensin transcript levels were significantly higher in samples from oxox transgenic plants relative to levels in control plants. Northern analysis revealed that sunflower defensin was induced in leaf tissue of the Sclerotinia-infected and oxox transgenic plants. A time course study showed that defensin, PR5-1 and BBE transcripts were highly induced in oxox-transgenic tissues at the 6-week-old stage. These results indicate that the defense pathways were activated in oxox transgenic sunflowers at that stage.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for increasing resistance of a plant to at least one pathogen, said method comprising transforming said plant with a DNA construct comprising a nucleotide sequence that encodes a protein having anti-pathogenic activity, wherein said nucleotide sequence is selected from the group consisting of:
   a) a nucleotide sequence encoding the amino acid sequence of SEQ ID:2;
   b) the nucleotide sequence set forth in SEQ ID:5;
   c) a nucleotide sequence that shares at least 95% sequence identity to the sequence of SEQ. ID:5; and
   d) the sunflower nucleotide sequence contained in a plasmid deposited as Patent Deposit No. PTA-73;

wherein said nucleotide sequence is operably linked to a promoter that drives expression of a coding sequence in a plant cell; and regenerating stably transformed plants with increased resistance to at least one pathogen.

2. The method of claim 1, wherein said pathogen is a fungal pathogen.

3. The method of claim 1, wherein said plant is a dicot.

4. The method of claim 1, wherein said plant is a monocot.

5. The method of claim 1, wherein said promoter is a constitutive promoter.

6. The method of claim 5, wherein said constitutive promoter is selected from the scp1 or ucp promoter.

7. The method of claim 1, wherein said promoter is an inducible promoter.

8. The method of claim 7, wherein said promoter is a pathogen-inducible promoter.

9. A plant having stably incorporated into its genome a DNA construct comprising a nucleotide sequence that encodes a protein having anti-pathogenic activity, wherein said nucleotide sequence is selected from the group consisting of:
   a) a nucleotide sequence encoding the amino acid sequence of SEQ ID:2;
   b) the nucleotide sequence set forth in SEQ ID:5;
   c) a nucleotide sequence that shares at least 95% sequence identity to the sequence of SEQ ID:5; and
   d) the sunflower nucleotide sequence contained in a plasmid deposited as Patent Deposit No. PTA-73;

wherein said nucleotide sequence is operably linked to a promoter that drives expression of a coding sequence in a plant cell.

10. Transformed seed of the plant according to claim 9.

11. A plant cell having stably incorporated into its genome a DNA construct comprising a nucleotide sequence that encodes a protein having anti-pathogenic activity, wherein said nucleotide sequence is selected from the group consisting of:
   a) a nucleotide sequence encoding the amino acid sequence of SEQ ID:2;
   b) the nucleotide sequence set forth in SEQ ID:5;
   c) a nucleotide sequence that shares at least 95% sequence identity to the sequence of SEQ ID:5; and,
   d) the sunflower-nucleotide sequence contained in a plasmid deposited as Patent Deposit No. PTA-73;

wherein said nucleotide sequence is operably linked to a promoter that drives expression of a coding sequence in a plant cell.

12. An isolated nucleic acid molecule having a nucleotide sequence that encodes a protein having anti-pathogenic activity, wherein said nucleotide sequence is selected from the group consisting of:
   a) a nucleotide sequence encoding the amino acid sequence of SEQ ID:2;
   b) the nucleotide sequence set forth in SEQ ID:5;
   c) a nucleotide sequence that shares at least 95% sequence identity to the sequence of SEQ ID:5; and
   d) the sunflower nucleotide sequence contained in a plasmid deposited as Patent Deposit No. PTA-73.

13. A DNA construct comprising a nucleotide sequence of claim 12.

14. A vector comprising the DNA construct of claim 13.

* * * * *

UNITED STATES PATENT AND TRADEMARK OFFICE
CERTIFICATE OF CORRECTION

PATENT NO. : 6,677,503 B1
DATED : January 13 2004
INVENTOR(S) : Bidney et al.

It is certified that error appears in the above-identified patent and that said Letters Patent is hereby corrected as shown below:

Title page,
Item [54], Title "ANTI-PATHOGENE" should read -- ANTI-PATHOGENIC --;
Item [73], Assignee:, the second Assignee's name, "GuraGen Corporation", should read -- CuraGen Corporation --.

Signed and Sealed this

Sixth Day of April, 2004

JON W. DUDAS
*Acting Director of the United States Patent and Trademark Office*

SEQUENCE LISTING

<160> NUMBER OF SEQ ID NOS: 41

<210> SEQ ID NO 1
<211> LENGTH: 222
<212> TYPE: PRT
<213> ORGANISM: Helianthus annuus

<400> SEQUENCE: 1

```
Met Thr Thr Ser Thr Leu Pro Thr Phe Leu Leu Leu Ala Ile Leu Phe
 1               5                  10                  15

His Tyr Thr Asn Ala Ala Val Phe Thr Ile Arg Asn Asn Cys Pro Tyr
            20                  25                  30

Thr Val Trp Ala Gly Ala Val Pro Gly Gly Gly Arg Gln Leu Asn Ser
        35                  40                  45

Gly Gln Thr Trp Ser Leu Thr Val Ala Ala Gly Thr Ala Gly Ala Arg
    50                  55                  60

Ile Trp Pro Arg Thr Asn Cys Asn Phe Asp Gly Ser Gly Arg Gly Arg
65                  70                  75                  80

Cys Gln Thr Gly Asp Cys Asn Gly Leu Leu Gln Cys Gln Asn Tyr Gly
                85                  90                  95

Thr Pro Pro Asn Thr Leu Ala Glu Tyr Ala Leu Asn Gln Phe Asn Asn
            100                 105                 110
```

-continued

```
Leu Asp Phe Phe Asp Ile Ser Leu Val Asp Gly Phe Asn Val Pro Met
            115                 120                 125
Val Phe Arg Pro Asn Ser Asn Gly Cys Thr Arg Gly Ile Ser Cys Thr
130                 135                 140
Ala Asp Ile Asn Gly Gln Cys Pro Gly Glu Leu Arg Ala Pro Gly Gly
145                 150                 155                 160
Cys Asn Asn Pro Cys Thr Val Tyr Lys Thr Asp Gln Tyr Cys Cys Asn
                165                 170                 175
Ser Gly Asn Cys Gly Pro Thr Asp Leu Ser Arg Phe Phe Lys Thr Arg
            180                 185                 190
Cys Pro Asp Ala Tyr Ser Tyr Pro Lys Asp Asp Pro Thr Ser Thr Phe
            195                 200                 205
Thr Cys Pro Gly Gly Thr Asn Tyr Asp Val Ile Phe Cys Pro
    210                 215                 220

<210> SEQ ID NO 2
<211> LENGTH: 542
<212> TYPE: PRT
<213> ORGANISM: Helianthus annuus

<400> SEQUENCE: 2

Met Asn Asn Ser Arg Ser Val Phe Leu Leu Val Leu Ala Leu Ser Phe
  1               5                  10                  15
Cys Val Ser Phe Gly Ala Leu Ser Ser Ile Phe Asp Val Thr Ser Thr
            20                  25                  30
Ser Glu Asp Phe Ile Thr Cys Leu Gln Ser Asn Ser Asn Asn Val Thr
        35                  40                  45
Thr Ile Ser Gln Leu Val Phe Thr Pro Ala Asn Thr Ser Tyr Ile Pro
 50                  55                  60
Ile Trp Gln Ala Ala Asp Pro Ile Arg Phe Asn Lys Ser Tyr Ile
 65                  70                  75                  80
Pro Lys Pro Ser Val Ile Val Thr Pro Thr Asp Glu Thr Gln Ile Gln
                85                  90                  95
Thr Ala Leu Leu Cys Ala Lys Lys His Gly Tyr Glu Phe Arg Ile Arg
            100                 105                 110
Asp Gly Gly His Asp Phe Glu Gly Asn Ser Tyr Thr Ala Asn Ala Pro
            115                 120                 125
Phe Val Met Leu Asp Leu Val Asn Met Arg Ala Ile Glu Ile Asn Val
130                 135                 140
Glu Asn Arg Thr Ala Leu Val Gln Gly Gly Ala Leu Leu Gly Glu Leu
145                 150                 155                 160
Tyr Tyr Thr Ile Ser Gln Lys Thr Asp Thr Leu Tyr Phe Pro Ala Gly
                165                 170                 175
Ile Trp Ala Gly Val Gly Val Ser Gly Phe Leu Ser Gly Gly Tyr
            180                 185                 190
Gly Asn Leu Leu Arg Lys Tyr Gly Leu Gly Ala Asp Asn Val Leu Asp
            195                 200                 205
Ile Arg Phe Met Asp Val Asn Gly Asn Ile Leu Asp Arg Lys Ser Met
    210                 215                 220
Gly Glu Asp Leu Phe Trp Ala Leu Arg Gly Gly Ala Ser Ser Phe
225                 230                 235                 240
Gly Ile Val Leu Gln Trp Lys Leu Asn Leu Val Pro Val Pro Glu Arg
                245                 250                 255
Val Thr Leu Phe Ser Val Ser Tyr Thr Leu Glu Gln Gly Ala Thr Asp
```

```
                260                 265                 270
Ile Phe His Lys Tyr Gln Tyr Val Leu Pro Lys Phe Asp Arg Asp Leu
                275                 280                 285

Leu Ile Arg Val Gln Leu Asn Thr Glu Tyr Ile Gly Asn Thr Thr Gln
            290                 295                 300

Lys Thr Val Arg Ile Leu Phe His Gly Ile Tyr Gln Gly Asn Ile Asp
305                 310                 315                 320

Thr Leu Leu Pro Leu Leu Asn Gln Ser Phe Pro Glu Leu Asn Val Thr
                325                 330                 335

Arg Glu Val Cys Gln Glu Val Arg Met Val Gln Thr Thr Leu Glu Phe
                340                 345                 350

Gly Gly Phe Asn Ile Ser Thr Pro Thr Ser Val Leu Ala Asn Arg Ser
            355                 360                 365

Ala Ile Pro Lys Leu Ser Phe Lys Gly Lys Ser Asp Tyr Val Arg Thr
        370                 375                 380

Pro Ile Pro Arg Ser Gly Leu Arg Lys Leu Trp Arg Lys Met Phe Glu
385                 390                 395                 400

Asn Asp Asn Ser Gln Thr Leu Phe Met Tyr Thr Phe Gly Gly Lys Met
                405                 410                 415

Glu Glu Tyr Ser Asp Thr Ala Ile Pro Tyr Pro His Arg Ala Gly Val
            420                 425                 430

Leu Tyr Gln Val Phe Lys Arg Val Asp Phe Val Asp Gln Pro Ser Asp
        435                 440                 445

Lys Thr Leu Ile Ser Leu Arg Arg Leu Ala Trp Leu Arg Ser Phe Asp
    450                 455                 460

Lys Thr Leu Glu Pro Tyr Val Thr Ser Asn Pro Arg Glu Ala Tyr Met
465                 470                 475                 480

Asn Tyr Asn Asp Leu Asp Leu Gly Phe Asp Ser Ala Ala Tyr Glu Glu
                485                 490                 495

Ala Ser Glu Trp Gly Glu Arg Tyr Trp Lys Arg Glu Asn Phe Lys Lys
            500                 505                 510

Leu Ile Arg Ile Lys Ala Lys Val Asp Pro Glu Asn Phe Phe Arg His
        515                 520                 525

Pro Gln Ser Ile Pro Val Phe Ser Arg Pro Leu Ser Asp Met
    530                 535                 540

<210> SEQ ID NO 3
<211> LENGTH: 108
<212> TYPE: PRT
<213> ORGANISM: Helianthus annuus

<400> SEQUENCE: 3

Met Ala Lys Ile Ser Val Ala Phe Asn Ala Phe Leu Leu Leu Leu Phe
1               5                   10                  15

Val Leu Ala Ile Ser Glu Ile Gly Ser Val Lys Gly Glu Leu Cys Glu
            20                  25                  30

Lys Ala Ser Gln Thr Trp Ser Gly Thr Cys Gly Lys Thr Lys His Cys
        35                  40                  45

Asp Asp Gln Cys Lys Ser Trp Glu Gly Ala Ala His Gly Ala Cys His
    50                  55                  60

Val Arg Asp Gly Lys His Met Cys Phe Cys Tyr Phe Asn Cys Ser Lys
65                  70                  75                  80

Ala Gln Lys Leu Ala Gln Asp Lys Leu Arg Ala Glu Glu Leu Ala Lys
                85                  90                  95
```

Glu Lys Ile Glu Pro Glu Lys Ala Thr Ala Lys Pro
            100                 105

<210> SEQ ID NO 4
<211> LENGTH: 875
<212> TYPE: DNA
<213> ORGANISM: Helianthus annuus

<400> SEQUENCE: 4

| | | | | | |
|---|---|---|---|---|---|
| atgacaacct | ccaccttcc | cactttcctt | ctcttggcta | ttctttttca | ctataccaat | 60 |
| gcagccgtgt | tcactattcg | aaacaactgt | ccatacaccg | tttgggctgg | tgcggtgcct | 120 |
| ggtggcggcc | gacaacttaa | ctcaggccaa | acctggtctt | taaccgtcgc | agctggcaca | 180 |
| gcaggagccc | gtatatggcc | ccgaaccaat | tgcaactttg | atggttctgg | gcgaggcagg | 240 |
| tgtcagaccg | gtgattgcaa | cggtctcctc | caatgccaaa | actatggtac | cccacccaac | 300 |
| acattggccg | agtacgcttt | gaaccagttc | aacaatcttg | atttctttga | catttctctt | 360 |
| gtggacggat | tcaatgtgcc | gatggtgttt | agacccaatt | ctaatgggtg | cacccggggt | 420 |
| atctcatgta | ctgcggatat | caatggccag | tgtcctggtg | agttacgggc | tcctggcggg | 480 |
| tgcaataacc | cttgcaccgt | gtacaaaact | gatcagtatt | gttgcaactc | tggaaattgt | 540 |
| ggaccaactg | atttatcaag | gttttttcaag | accagatgtc | ctgatgcata | tagttatccc | 600 |
| aaggatgatc | caactagcac | atttacgtgc | cccggtggaa | ccaactacga | cgttatattc | 660 |
| tgcccttgat | caaagccatt | tgattatatg | atcaaattaa | aaggagttcg | aaatataaga | 720 |
| actgaaataa | atggagtgaa | taagtaatgg | agatagtcta | attataaggc | ttcttcctca | 780 |
| ttgtaataca | ataatgttgt | aatttgtcaa | aataaatgga | tggatatata | tgattaatta | 840 |
| ttaggaaaaa | aaaaaaaaaa | aaaaaaaaaa | aaaaa | | | 875 |

<210> SEQ ID NO 5
<211> LENGTH: 1809
<212> TYPE: DNA
<213> ORGANISM: Helianthus annuus

<400> SEQUENCE: 5

| | | | | | |
|---|---|---|---|---|---|
| aaaacatgaa | taactctcgt | tcagtgttcc | tcttagttct | cgctctttca | ttttgtgttt | 60 |
| catttggagc | attgtcttcc | attttcgatg | ttacttcaac | ttccgaagat | ttcataacct | 120 |
| gtctccaatc | caattccaac | aatgtccacca | ccatctctca | actcgttttc | accccggcca | 180 |
| acacttctta | catacccatt | tggcaagctg | cagccgaccc | tattcggttc | aacaaatcct | 240 |
| acattccgaa | accatcagtc | atcgttactc | ccaccgatga | acacagatc | caaaccgctc | 300 |
| tttatatgcgc | caagaaacac | ggatatgagt | ttaggatccg | agacggtggt | catgacttcg | 360 |
| agggcaactc | atacaccgcg | aacgctccgt | tgtcatgct | tgatctcgtc | aacatgaggg | 420 |
| ctatagagat | caacgttgaa | aaccggaccg | cgctggtcca | gggtggcgct | ttgcttggtg | 480 |
| agctctacta | cactatttct | cagaaaacgg | acaccttgta | ttttcctgct | ggtatttggg | 540 |
| ccggtgtggg | tgttagcggg | ttttttgagcg | gtggtgggta | tggaaacctg | ttgaggaaat | 600 |
| acgggcttgg | tgccgataat | gttttggata | ttcgtttcat | ggatgttaat | ggaaacattc | 660 |
| ttgataggaa | atcgatgggc | gaagatttgt | tttgggcgct | tcgtggcggt | ggtgcttcca | 720 |
| gtttcggaat | tgttctccag | tggaagctca | atttggttcc | ggtgcctgaa | agagttactc | 780 |
| ttttcagtgt | gagttatact | ctggagcaag | ggcgacgga | cattttccat | aaatatcaat | 840 |
| acgtgttacc | gaaatttgat | cgtgatttac | tcatcagagt | tcagcttaac | accgagtata | 900 |

-continued

| | |
|---|---|
| taggcaacac cactcagaaa accgtacgaa tattgtttca cggtatttat caaggcaata | 960 |
| ttgacacact gcttccgttg ttgaaccaaa gtttcccaga gctcaatgtg acacgagaag | 1020 |
| tctgccaaga agtacgaatg gtccagacta cccttgagtt tggaggcttt aacatctcta | 1080 |
| ccccgacatc ggttctagcg aaccgatcag caatccccaa gctgagcttc aaggaaaat | 1140 |
| ctgactatgt ccgaactcca attcccagaa gcgggctaag aaagctctgg agaaagatgt | 1200 |
| tgaaaacga caactcacag actctcttca tgtacacatt tggtgggaag atggaggagt | 1260 |
| actcagatac agcaattccg tatccccata gagctggggt gttgtaccaa gtgttcaaga | 1320 |
| gggtggactt cgtggatcag ccttcggaca agaccttgat atcactcaga cggttagctt | 1380 |
| ggctccgaag ctttgataag actttggagc cgtacgtgac gagtaacccg agggaggcgt | 1440 |
| atatgaacta caatgatctt gatttggtt ttgatagtgc tgcatatgaa gaagcaagtg | 1500 |
| aatggggaga aggtattgg aaagggaga actttaagaa gttgatccga atcaaggcta | 1560 |
| aagttgatcc ggaaaatttc tttagacacc cacaaagtat accggttttc tcaagacctc | 1620 |
| tctcagatat gtgaagccaa cactttggat ggtgttcttt ttcttgagta tattggtaat | 1680 |
| aattattaat taagagtcaa aagtcgatta cttttgtgtt tggtgccttg tgtaccaatt | 1740 |
| attttaaactt ttttgttttc ataaactttt aatcaaagct attatgtatt taaaaaaaaa | 1800 |
| aaaaaaaaa | 1809 |

<210> SEQ ID NO 6
<211> LENGTH: 565
<212> TYPE: DNA
<213> ORGANISM: Helianthus annuus

<400> SEQUENCE: 6

| | |
|---|---|
| tcggcttgag cttgagctta gttcagtaac ttaaaaatgg ccaaaatttc agttgctttc | 60 |
| aatgcttttc ttctgcttct ctttgttctt gctatctcag aaatcggatc ggtgaaagga | 120 |
| gaattatgtg agaaggcaag ccagacatgg tccggaacat gtggcaagac aaaacactgt | 180 |
| gatgaccagt gcaagtcttg ggagggtgca gcccatggag cttgtcacgt gcgcgatggg | 240 |
| aaacacatgt gcttctgcta cttcaactgt tccaaagccc agaagttggc tcaggataaa | 300 |
| ctcagagcgg aagagctcgc caaggagaag attgaaccg aaaaggcgac agccaaacct | 360 |
| tgagtatgta gcaaatgtca tacgattatg aataaagaga aaatgctttc tacttggcat | 420 |
| attcagcatt tccttgtgtg taatgttttgt tgtatttgga aattggaatc agttgcttca | 480 |
| ttatgattcc atgcaaaatg ttctaatgaa atgatattta aattaaaaaa aaaaaaaaaa | 540 |
| aaaaaaaaaa aaaaaaaaaa aaaaa | 565 |

<210> SEQ ID NO 7
<211> LENGTH: 550
<212> TYPE: DNA
<213> ORGANISM: Helianthus annuus

<400> SEQUENCE: 7

| | |
|---|---|
| aaaactgcgt tttgaaaagg catgtaggta catgcttctc caaaactgcg ttttgaaggc | 60 |
| agataatcac ttttcatcca acatttttt tagattattt atgttttaca aacgcaatac | 120 |
| ttaaataacc acttcaaaac gtaatcccaa acaccctctt agtgtataaa aaacctgaaa | 180 |
| ttagtttata cacacagaaa ataacaaatt aaaagcataa acaaaaatga taattttata | 240 |
| aatgataaac aaaactaagt ataagaataa gataatatat atttttata gagttactaa | 300 |
| atacaaagat aaaataacaa aaagagtaa actaaaataa gttataacaa atgtgttgtt | 360 |

```
aactgtatag ttatgacttt gtctactaca gaacaattcc acgtaaccat tttgttcaat    420
gaatacattt gaaatttcaa tgaatgtata tctttctaaa tattgtacgt atagcatgtt    480
cggcctatat aaaccatgtt tactctcact tccaattcac ccaaaaccac aatgacaacc    540
tccacccttc                                                          550
```

<210> SEQ ID NO 8
<211> LENGTH: 351
<212> TYPE: DNA
<213> ORGANISM: Helianthus annuus
<400> SEQUENCE: 8

```
tgttcaaaaa agcacgctga aagtgactaa tattcgaatc tagtcgtgac cgctgcctag     60
tgccaaatta ctaaggaga agaaaaaaaa aatatcaaga agatacagaa aattatttgc    120
gcgttgtgac ttgtgttgtg taggcaacgg gcatctagtc atacatttga tggctgtttc    180
ggtgtaaaca taagtcaaag gctagatgtc tttttatcaa aaaggttgtt ttagtaattt    240
cccaaaaaaa catcccactt tcccccttat ttcttcccaa tcgccttcgg gttcatctta    300
tataaatagg cgcattaagt gctaatagac tcaccaaacc aacaaaacat g            351
```

<210> SEQ ID NO 9
<211> LENGTH: 1346
<212> TYPE: DNA
<213> ORGANISM: Helianthus annuus
<400> SEQUENCE: 9

```
gtacttcgca aaagggcctg tcgtaaatgt tagtgagatg ggcaatcgtc tcaacgtcaa     60
tatttagcga ccataatttg tcagaaaatt aacgacagga actaaattga ttgcaaattt    120
agcaaccaaa ataatcagtc tgaaagtaat tagcaattaa acaaaattgg tggtaaattt    180
acaacgattt ttttttacaat gatttattgt tattttttac ttgacctgac tactgagttg    240
ttttaacctt aatcatttct atcagagtga ataaagcctc catggcacag aaaaaatgta    300
agaattatat gaatacagat aattacgata atttctgta taaataggtg gtttaggaaa    360
actattaagc cctgttgttt tgcatctgaa tagaatcaat cagaggttgg ctctgattca    420
atcagaactc aaaagttttg gtgtttggtt cgacatctga atgacatcta aatggggatt    480
tcaagctctt aactattcag ctttgaggag tcgctaaacc attagagga tttctgatat     540 tacatgtaaa aattaagcaa agtcacgtgc atgtgtatat gaatgaattt catcaaagtc    600
gcgtgcaagt gtatatgtta tgtgaatggt cctgtatcta atatacaaac atatgtttac    660
atgcaatttc aaaaatgccc taaccacgt agtgacacaa aaaaaaaaaa aaaagtttgc    720
taacttatga agttacttg gatgtataca atgcacgcac cacaaagtc aatttaagac      780 aaattttgtg gaactttag ccatttttgtg tttattgtt attgtttatt tcttgactt       840 tcaacatatt ttctcctata aatacccctc attgtctcat cttctcttca caaaccttgc    900
aacaagtgtt cttgagctta gttcagtaac taaaaaatgg ccaaaagtgc agttgctttc    960
tatgcttttc ttctgcttct ctttgttctt gctatctcag gttctcaatc aatcttattt   1020
acactcactt tgtgttcgta atattcagac ttttacacct taatgtcaca tattttgacc   1080
cttcggatga caattagttt agttaagtag accgtgacat taagctagca ctcatactta   1140
aataatgcag tgaaagaag catttttataa gtatataaaa gtgatttaat tagcttttat   1200
ttcgtgcaga aactaatcat attcatcaca aaactgcatt cgttagacat tctagatttg   1260
```

```
tgtataacgt acttaacaca gtttaacgtg tacagaaatc ggatcggtga aggagaatt        1320 atgtgagaag gcaagccaga catgtc                                           1346
```

<210> SEQ ID NO 10
<211> LENGTH: 225
<212> TYPE: PRT
<213> ORGANISM: Vitis vinifera

<400> SEQUENCE: 10

```
Met Gly Leu Cys Lys Ile Leu Ser Ile Ser Ser Phe Leu Leu Thr Thr
 1               5                  10                  15
Leu Phe Phe Thr Ser Ser Tyr Ala Ala Thr Phe Asn Ile Gln Asn His
            20                  25                  30
Cys Ser Tyr Thr Val Trp Ala Ala Val Pro Gly Gly Met Gln
        35                  40                  45
Leu Gly Ser Gly Gln Ser Trp Ser Leu Asn Val Asn Ala Gly Thr Thr
    50                  55                  60
Gly Ala Arg Val Trp Gly Arg Thr Asn Cys Asn Phe Asp Ala Ser Gly
65                  70                  75                  80
Asn Gly Lys Cys Glu Thr Gly Asp Cys Gly Gly Leu Leu Gln Cys Thr
                85                  90                  95
Ala Tyr Gly Thr Pro Pro Asn Thr Leu Ala Glu Phe Ala Leu Asn Gln
            100                 105                 110
Phe Ser Asn Leu Asp Phe Phe Asp Ile Ser Leu Val Asp Gly Phe Asn
        115                 120                 125
Val Pro Met Ala Phe Asn Pro Thr Ser Asn Gly Cys Thr Arg Gly Ile
    130                 135                 140
Ser Cys Thr Ala Asp Ile Val Gly Glu Cys Pro Ala Ala Leu Lys Thr
145                 150                 155                 160
Thr Gly Gly Cys Asn Asn Pro Cys Thr Val Phe Lys Thr Asp Glu Tyr
                165                 170                 175
Cys Cys Asn Ser Gly Ser Cys Asn Ala Thr Thr Tyr Ser Glu Phe Phe
            180                 185                 190
Lys Thr Arg Cys Pro Asp Ala Tyr Ser Tyr Pro Lys Asp Asp Gln Thr
        195                 200                 205
Ser Thr Phe Thr Cys Pro Ala Gly Thr Asn Tyr Glu Val Ile Phe Cys
    210                 215                 220
Pro
225
```

<210> SEQ ID NO 11
<211> LENGTH: 222
<212> TYPE: PRT
<213> ORGANISM: Vitis vinifera

<400> SEQUENCE: 11

```
Met Arg Phe Thr Thr Thr Leu Pro Ile Leu Ile Pro Leu Leu Leu Ser
 1               5                  10                  15
Leu Leu Phe Thr Ser Thr His Ala Ala Thr Phe Asp Ile Leu Asn Lys
            20                  25                  30
Cys Thr Tyr Thr Val Trp Ala Ala Ala Ser Pro Gly Gly Gly Arg Arg
        35                  40                  45
Leu Asp Ser Gly Gln Ser Trp Thr Ile Thr Val Asn Pro Gly Thr Thr
    50                  55                  60
Asn Ala Arg Ile Trp Gly Arg Thr Ser Cys Thr Phe Asp Ala Asn Gly
65                  70                  75                  80
```

```
Arg Gly Lys Cys Glu Thr Gly Asp Cys Asn Gly Leu Leu Glu Cys Gln
                85                  90                  95

Gly Tyr Gly Ser Pro Pro Asn Thr Leu Ala Glu Phe Ala Leu Asn Gln
            100                 105                 110

Pro Asn Asn Leu Asp Tyr Ile Asp Ile Ser Leu Val Asp Gly Phe Asn
        115                 120                 125

Ile Pro Met Asp Phe Ser Gly Cys Arg Gly Ile Gln Cys Ser Val Asp
    130                 135                 140

Ile Asn Gly Gln Cys Pro Ser Glu Leu Lys Ala Pro Gly Gly Cys Asn
145                 150                 155                 160

Asn Pro Cys Thr Val Phe Lys Thr Asn Glu Tyr Cys Cys Thr Asp Gly
                165                 170                 175

Pro Gly Ser Cys Gly Pro Thr Thr Tyr Ser Lys Phe Phe Lys Asp Arg
            180                 185                 190

Cys Pro Asp Ala Tyr Ser Tyr Pro Gln Asp Asp Lys Thr Ser Leu Phe
        195                 200                 205

Thr Cys Pro Ser Gly Thr Asn Tyr Lys Val Thr Phe Cys Pro
    210                 215                 220

<210> SEQ ID NO 12
<211> LENGTH: 202
<212> TYPE: PRT
<213> ORGANISM: Glycine Max

<400> SEQUENCE: 12

Ala Arg Phe Glu Ile Thr Asn Arg Cys Thr Tyr Thr Val Trp Ala Ala
1               5                   10                  15

Ser Val Pro Val Gly Gly Val Gln Leu Asn Pro Gly Gln Ser Trp
            20                  25                  30

Ser Val Asp Val Pro Ala Gly Thr Lys Gly Ala Arg Val Trp Ala Arg
        35                  40                  45

Thr Gly Cys Asn Phe Asp Gly Ser Gly Arg Gly Gly Cys Gln Thr Gly
    50                  55                  60

Asp Cys Gly Gly Val Leu Asp Cys Lys Ala Tyr Gly Ala Pro Pro Asn
65                  70                  75                  80

Thr Leu Ala Glu Tyr Gly Leu Asn Gly Phe Asn Asn Leu Asp Phe Phe
                85                  90                  95

Asp Ile Ser Leu Val Asp Gly Phe Asn Val Pro Met Asp Phe Ser Pro
            100                 105                 110

Thr Ser Asn Gly Cys Thr Arg Gly Ile Ser Cys Thr Ala Asp Ile Asn
        115                 120                 125

Gly Gln Cys Pro Ser Glu Leu Lys Thr Gln Gly Gly Cys Asn Asn Pro
    130                 135                 140

Cys Thr Val Phe Lys Thr Asp Gln Tyr Cys Cys Asn Ser Gly Ser Cys
145                 150                 155                 160

Gly Pro Thr Asp Tyr Ser Arg Phe Phe Lys Gln Arg Cys Pro Asp Ala
                165                 170                 175

Tyr Ser Tyr Pro Lys Asp Asp Pro Ser Thr Phe Thr Cys Asn Gly
            180                 185                 190

Gly Thr Asp Tyr Arg Val Val Phe Cys Pro
        195                 200

<210> SEQ ID NO 13
<211> LENGTH: 223
<212> TYPE: PRT
```

<213> ORGANISM: Helainthus annuus

<400> SEQUENCE: 13

Met Thr Thr Ser Thr Leu Pro Thr Phe Leu Leu Ala Ile Leu Phe
 1               5                  10                  15

His Tyr Thr Asn Ala Ala Val Phe Thr Ile Arg Asn Asn Cys Pro Tyr
             20                  25                  30

Thr Val Trp Ala Gly Ala Val Pro Gly Gly Arg Gln Leu Asn Ser
         35                  40                  45

Gly Gln Thr Trp Ser Leu Thr Val Ala Ala Gly Thr Ala Gly Ala Arg
     50                  55                  60

Ile Trp Pro Arg Thr Asn Cys Asn Phe Asp Gly Ser Gly Arg Gly Arg
65                  70                  75                  80

Cys Gln Thr Gly Asp Cys Asn Gly Leu Leu Gln Cys Gln Asn Tyr Gly
                 85                  90                  95

Thr Pro Pro Asn Thr Phe Gly Ser Glu Tyr Ala Leu Asn Gln Phe Asn
                100                 105                 110

Asn Leu Asp Phe Phe Asp Ile Ser Leu Val Asp Gly Phe Asn Val Pro
                115                 120                 125

Met Val Phe Arg Pro Asn Ser Asn Gly Cys Thr Arg Gly Ile Ser Cys
        130                 135                 140

Thr Ala Asp Ile Asn Gly Gln Cys Pro Gly Glu Leu Arg Ala Pro Gly
145                 150                 155                 160

Gly Cys Asn Asn Pro Cys Thr Val Tyr Lys Thr Asp Gln Tyr Cys Cys
                165                 170                 175

Asn Ser Gly Asn Cys Gly Pro Thr Asp Leu Ser Arg Phe Phe Lys Thr
            180                 185                 190

Arg Cys Pro Asp Ala Tyr Ser Tyr Pro Lys Asp Asp Pro Thr Ser Thr
        195                 200                 205

Phe Thr Cys Pro Gly Gly Thr Asn Tyr Asp Val Ile Phe Cys Pro
    210                 215                 220

<210> SEQ ID NO 14
<211> LENGTH: 238
<212> TYPE: PRT
<213> ORGANISM: Lycopersicon esculentum

<400> SEQUENCE: 14

Phe Phe Phe Leu Leu Ala Phe Val Thr Tyr Thr Tyr Ala Ala Thr Phe
 1               5                  10                  15

Glu Val Arg Asn Asn Cys Pro Tyr Thr Val Trp Ala Ala Ser Thr Pro
             20                  25                  30

Ile Gly Gly Gly Arg Arg Leu Asp Arg Gly Gln Thr Trp Val Ile Asn
         35                  40                  45

Ala Pro Arg Gly Thr Lys Met Ala Arg Ile Trp Gly Arg Thr Asn Cys
     50                  55                  60

Asn Phe Asp Gly Asp Gly Arg Gly Ser Cys Gln Thr Gly Asp Cys Gly
65                  70                  75                  80

Gly Val Leu Gln Cys Thr Gly Trp Gly Lys Pro Pro Asn Thr Leu Ala
                 85                  90                  95

Glu Tyr Ala Leu Asp Gln Phe Ser Asn Leu Asp Phe Trp Asp Ile Ser
                100                 105                 110

Leu Val Asp Gly Phe Asn Ile Pro Met Thr Phe Ala Pro Thr Asn Pro
                115                 120                 125

Ser Gly Gly Lys Cys His Ala Ile His Cys Thr Ala Asn Ile Asn Gly

```
              130                 135                 140
Glu Cys Pro Gly Ser Leu Arg Val Pro Gly Gly Cys Asn Asn Pro Cys
145                 150                 155                 160

Thr Thr Phe Gly Gly Gln Gln Tyr Cys Cys Thr Gln Gly Pro Cys Gly
                165                 170                 175

Pro Thr Asp Leu Ser Arg Phe Phe Lys Gln Arg Cys Pro Asp Ala Tyr
            180                 185                 190

Ser Tyr Pro Gln Asp Asp Pro Thr Ser Thr Phe Thr Cys Pro Ser Gly
        195                 200                 205

Ser Thr Asn Tyr Arg Val Val Phe Cys Pro Asn Gly Val Thr Ser Pro
    210                 215                 220

Asn Phe Pro Leu Glu Met Pro Ser Ser Asp Glu Glu Ala Lys
225                 230                 235

<210> SEQ ID NO 15
<211> LENGTH: 246
<212> TYPE: PRT
<213> ORGANISM: Solanum commersonii

<400> SEQUENCE: 15

Met Ala Tyr Leu Arg Ser Ser Phe Val Phe Leu Leu Ala Phe Val
1               5                   10                  15

Thr Tyr Thr Tyr Ala Ala Thr Ile Glu Val Arg Asn Asn Cys Pro Tyr
                20                  25                  30

Thr Val Trp Ala Ala Ser Thr Pro Ile Gly Gly Gly Arg Arg Leu Asp
            35                  40                  45

Arg Gly Gln Thr Trp Val Ile Asn Ala Pro Arg Gly Thr Lys Met Ala
        50                  55                  60

Arg Ile Trp Gly Arg Thr Asn Cys Asn Phe Asp Gly Ala Gly Arg Gly
65                  70                  75                  80

Ser Cys Gln Thr Gly Asp Cys Gly Gly Val Leu Gln Cys Thr Gly Trp
                85                  90                  95

Gly Lys Pro Pro Asn Thr Leu Ala Glu Tyr Ala Leu Asp Gln Phe Ser
            100                 105                 110

Asn Leu Asp Phe Trp Asp Ile Ser Leu Val Asp Gly Phe Asn Ile Pro
        115                 120                 125

Met Thr Phe Ala Pro Thr Asn Pro Ser Gly Gly Lys Cys His Ala Ile
    130                 135                 140

His Cys Thr Ala Asn Ile Asn Gly Glu Cys Pro Gly Ser Leu Arg Val
145                 150                 155                 160

Pro Gly Gly Cys Asn Asn Pro Cys Thr Thr Phe Gly Gly Gln Gln Tyr
                165                 170                 175

Cys Cys Thr Gln Gly Pro Cys Gly Pro Thr Asp Leu Ser Arg Phe Phe
            180                 185                 190

Lys Gln Arg Cys Pro Asp Ala Tyr Ser Tyr Pro Gln Asp Asp Pro Thr
        195                 200                 205

Ser Thr Phe Thr Cys Pro Ser Gly Ser Thr Asn Tyr Arg Val Val Phe
    210                 215                 220

Cys Pro Asn Gly Val Thr Ser Pro Asn Phe Pro Leu Glu Met Pro Ala
225                 230                 235                 240

Ser Asp Glu Glu Ala Lys
                245

<210> SEQ ID NO 16
<211> LENGTH: 529
```

```
<212> TYPE: PRT
<213> ORGANISM: Helianthus annuus

<400> SEQUENCE: 16

Met Glu Thr Ser Ile Leu Thr Leu Leu Leu Leu Leu Ser Thr Gln
 1               5                  10                  15

Ser Ser Ala Thr Ser Arg Ser Ile Thr Asp Arg Phe Ile Gln Cys Leu
             20                  25                  30

His Asp Arg Ala Asp Pro Ser Phe Pro Ile Thr Gly Glu Val Tyr Thr
             35                  40                  45

Pro Gly Asn Ser Ser Phe Pro Thr Val Leu Gln Asn Tyr Ile Arg Asn
     50                  55                  60

Leu Arg Phe Asn Glu Thr Thr Thr Pro Lys Pro Phe Leu Ile Ile Thr
65                   70                  75                  80

Ala Glu His Val Ser His Ile Gln Ala Ala Val Val Cys Gly Lys Gln
                 85                  90                  95

Asn Arg Leu Leu Leu Lys Thr Arg Ser Gly Gly His Asp Tyr Glu Gly
                100                 105                 110

Leu Ser Tyr Leu Thr Asn Thr Asn Gln Pro Phe Ile Val Asp Met
            115                 120                 125

Phe Asn Leu Arg Ser Ile Asn Val Asp Ile Glu Gln Glu Thr Ala Trp
130                 135                 140

Val Gln Ala Gly Ala Thr Leu Gly Glu Val Tyr Tyr Arg Ile Ala Glu
145                 150                 155                 160

Lys Ser Asn Lys His Gly Phe Pro Ala Gly Val Cys Pro Thr Val Gly
                165                 170                 175

Val Gly Gly His Phe Ser Gly Gly Gly Tyr Gly Asn Leu Met Arg Lys
            180                 185                 190

Tyr Gly Leu Ser Val Asp Asn Ile Val Asp Ala Gln Ile Ile Asp Val
            195                 200                 205

Asn Gly Lys Leu Leu Asp Arg Lys Ser Met Gly Glu Asp Leu Phe Trp
    210                 215                 220

Ala Tyr Thr Gly Gly Gly Gly Val Ser Phe Gly Val Val Leu Ala Tyr
225                 230                 235                 240

Lys Ile Lys Leu Val Arg Val Pro Glu Val Val Thr Val Phe Thr Ile
                245                 250                 255

Glu Arg Arg Glu Glu Gln Asn Leu Ser Thr Ile Ala Glu Arg Trp Val
            260                 265                 270

Gln Val Ala Asp Lys Leu Asp Arg Asp Leu Phe Leu Arg Met Thr Phe
            275                 280                 285

Ser Val Ile Asn Asp Thr Asn Gly Gly Lys Thr Val Arg Ala Ile Phe
    290                 295                 300

Pro Thr Leu Tyr Leu Gly Asn Ser Arg Asn Leu Val Thr Leu Leu Asn
305                 310                 315                 320

Lys Asp Phe Pro Glu Leu Gly Leu Gln Glu Ser Asp Cys Thr Glu Met
                325                 330                 335

Ser Trp Val Glu Ser Val Leu Tyr Tyr Thr Gly Phe Pro Ser Gly Thr
            340                 345                 350

Pro Thr Thr Ala Leu Leu Ser Arg Thr Pro Gln Arg Leu Asn Pro Phe
            355                 360                 365

Lys Ile Lys Ser Asp Tyr Val Gln Asn Pro Ile Ser Lys Arg Gln Phe
    370                 375                 380

Glu Phe Ile Phe Glu Arg Met Lys Glu Leu Glu Asn Gln Met Leu Ala
385                 390                 395                 400
```

```
Phe Asn Pro Tyr Gly Gly Arg Met Ser Glu Ile Ser Glu Phe Ala Lys
            405                 410                 415

Pro Phe Pro His Arg Ser Gly Asn Ile Ala Lys Ile Gln Tyr Glu Val
            420                 425                 430

Asn Trp Glu Asp Leu Ser Asp Glu Ala Glu Asn Arg Tyr Leu Asn Phe
            435                 440                 445

Thr Arg Leu Met Tyr Asp Tyr Met Thr Pro Phe Val Ser Lys Asn Pro
            450                 455                 460

Arg Glu Ala Phe Leu Asn Tyr Arg Asp Leu Asp Ile Gly Ile Asn Ser
465                 470                 475                 480

His Gly Arg Asn Ala Tyr Thr Glu Gly Met Val Tyr Gly His Lys Tyr
                485                 490                 495

Phe Lys Glu Thr Asn Tyr Lys Arg Leu Val Ser Val Lys Thr Lys Val
            500                 505                 510

Asp Pro Asp Asn Phe Phe Arg Asn Glu Gln Ser Ile Pro Thr Leu Ser
            515                 520                 525

Ser

<210> SEQ ID NO 17
<211> LENGTH: 529
<212> TYPE: PRT
<213> ORGANISM: Healianthus annuus

<400> SEQUENCE: 17

Met Gln Thr Ser Ile Leu Thr Leu Leu Leu Leu Leu Ser Thr Gln
1               5                   10                  15

Ser Ser Ala Thr Ser Arg Ser Ile Thr Asp Arg Phe Ile Gln Cys Leu
            20                  25                  30

His Asp Arg Ala Asp Pro Ser Phe Pro Ile Thr Gly Glu Val Tyr Thr
            35                  40                  45

Pro Gly Asn Ser Ser Phe Pro Thr Val Leu Gln Asn Tyr Ile Arg Asn
        50                  55                  60

Leu Arg Phe Asn Glu Thr Thr Thr Pro Lys Pro Phe Leu Ile Ile Thr
65                  70                  75                  80

Ala Glu His Val Ser His Ile Gln Ala Ala Val Val Cys Gly Lys Gln
                85                  90                  95

Asn Arg Leu Leu Leu Lys Thr Arg Ser Gly His Asp Tyr Glu Gly
            100                 105                 110

Leu Ser Tyr Leu Thr Asn Thr Asn Gln Pro Phe Phe Ile Val Asp Met
            115                 120                 125

Phe Asn Leu Arg Ser Ile Asn Ile Asp Ile Glu Gln Glu Thr Ala Trp
            130                 135                 140

Val Gln Ala Gly Ala Thr Leu Gly Glu Val Tyr Tyr Arg Ile Ala Glu
145                 150                 155                 160

Lys Ser Asn Lys His Gly Phe Pro Ala Gly Val Cys Pro Thr Val Gly
                165                 170                 175

Val Gly Gly His Phe Ser Gly Gly Gly Tyr Gly Asn Leu Met Arg Lys
            180                 185                 190

Tyr Gly Leu Ser Val Asp Asn Ile Val Asp Ala Gln Ile Ile Asp Val
            195                 200                 205

Asn Gly Lys Leu Leu Asp Arg Lys Ser Met Gly Glu Asp Leu Phe Trp
        210                 215                 220

Ala Ile Thr Gly Gly Gly Gly Val Ser Phe Gly Val Val Leu Ala Tyr
225                 230                 235                 240
```

-continued

```
Lys Ile Lys Leu Val Arg Val Pro Glu Val Val Thr Val Phe Thr Ile
                245                 250                 255
Glu Arg Arg Glu Glu Gln Asn Leu Ser Thr Ile Ala Glu Arg Trp Val
            260                 265                 270
Gln Val Ala Asp Lys Leu Asp Arg Asp Leu Phe Leu Arg Met Thr Phe
        275                 280                 285
Ser Val Ile Asn Asp Thr Asn Gly Gly Lys Thr Val Arg Ala Ile Phe
    290                 295                 300
Pro Thr Leu Tyr Leu Gly Asn Ser Arg Asn Leu Val Thr Leu Leu Asn
305                 310                 315                 320
Lys Asp Phe Pro Glu Leu Gly Leu Gln Glu Ser Asp Cys Thr Glu Met
                325                 330                 335
Ser Trp Val Glu Ser Val Leu Tyr Tyr Thr Gly Phe Pro Ser Gly Thr
            340                 345                 350
Pro Thr Thr Ala Leu Leu Ser Arg Thr Pro Gln Arg Leu Asn Pro Phe
        355                 360                 365
Lys Ile Lys Ser Asp Tyr Val Gln Asn Pro Ile Ser Lys Arg Gln Phe
    370                 375                 380
Glu Phe Ile Phe Glu Arg Leu Lys Glu Leu Glu Asn Gln Met Leu Ala
385                 390                 395                 400
Phe Asn Pro Tyr Gly Gly Arg Met Ser Glu Ile Ser Glu Phe Ala Lys
                405                 410                 415
Pro Phe Pro His Arg Ser Gly Asn Ile Ala Lys Ile Gln Tyr Glu Val
            420                 425                 430
Asn Trp Glu Asp Leu Ser Asp Glu Ala Glu Asn Arg Tyr Leu Asn Phe
        435                 440                 445
Thr Arg Leu Met Tyr Asp Tyr Met Thr Pro Phe Val Ser Lys Asn Pro
    450                 455                 460
Arg Lys Ala Phe Leu Asn Tyr Arg Asp Leu Asp Ile Gly Ile Asn Ser
465                 470                 475                 480
His Gly Arg Asn Ala Tyr Thr Glu Gly Met Val Tyr Gly His Lys Tyr
                485                 490                 495
Phe Lys Glu Thr Asn Tyr Lys Arg Leu Val Ser Val Lys Thr Lys Val
            500                 505                 510
Asp Pro Asp Asn Phe Phe Arg Asn Glu Gln Ser Ile Pro Thr Leu Ser
        515                 520                 525
Ser
```

<210> SEQ ID NO 18
<211> LENGTH: 535
<212> TYPE: PRT
<213> ORGANISM: Papaver somniferum

<400> SEQUENCE: 18

```
Met Met Cys Arg Ser Leu Thr Leu Arg Phe Phe Leu Phe Ile Val Leu
  1               5                  10                  15
Leu Gln Thr Cys Val Arg Gly Gly Asp Val Asn Asp Asn Leu Leu Ser
                20                  25                  30
Ser Cys Leu Asn Ser His Gly Val His Asn Phe Thr Thr Leu Ser Thr
            35                  40                  45
Asp Thr Asn Ser Asp Tyr Phe Lys Leu Leu His Ala Ser Met Gln Asn
        50                  55                  60
Pro Leu Phe Ala Lys Pro Thr Val Ser Lys Pro Ser Phe Ile Val Met
65                  70                  75                  80
```

```
Pro Gly Ser Lys Glu Glu Leu Ser Ser Thr Val His Cys Cys Thr Arg
                85                  90                  95
Glu Ser Trp Thr Ile Arg Leu Arg Ser Gly His Ser Tyr Glu Gly
            100                 105                 110
Leu Ser Tyr Thr Ala Asp Thr Pro Phe Val Ile Val Asp Met Met Asn
            115                 120                 125
Leu Asn Arg Ile Ser Ile Asp Val Leu Ser Glu Thr Ala Trp Val Glu
        130                 135                 140
Ser Gly Ala Thr Leu Gly Glu Leu Tyr Tyr Ala Ile Ala Gln Ser Thr
145                 150                 155                 160
Asp Thr Leu Gly Phe Thr Ala Gly Trp Cys Pro Thr Val Gly Ser Gly
                165                 170                 175
Gly His Ile Ser Gly Gly Phe Gly Met Met Ser Arg Lys Tyr Gly
                180                 185                 190
Leu Ala Ala Asp Asn Val Val Asp Ala Ile Leu Ile Asp Ser Asn Gly
            195                 200                 205
Ala Ile Leu Asp Arg Glu Lys Met Gly Asp Asp Val Phe Trp Ala Ile
        210                 215                 220
Arg Gly Gly Gly Gly Val Trp Gly Ala Ile Tyr Ala Trp Lys Ile
225                 230                 235                 240
Lys Leu Leu Pro Val Pro Glu Lys Leu Thr Val Phe Arg Val Thr Lys
                245                 250                 255
Asn Val Gly Ile Glu Asp Ala Ser Ser Leu Leu His Lys Trp Gln Tyr
                260                 265                 270
Val Ala Asp Glu Leu Asp Glu Asp Phe Thr Val Ser Val Leu Gly Gly
            275                 280                 285
Val Asn Gly Asn Asp Ala Trp Leu Met Phe Leu Gly Leu His Leu Gly
        290                 295                 300
Arg Lys Asp Ala Ala Lys Thr Ile Ile Asp Glu Lys Phe Pro Glu Leu
305                 310                 315                 320
Gly Leu Val Asp Lys Glu Phe Gln Glu Met Ser Trp Gly Glu Ser Met
                325                 330                 335
Ala Phe Leu Ser Gly Leu Asp Thr Ile Ser Glu Leu Asn Asn Arg Phe
                340                 345                 350
Leu Lys Phe Asp Glu Arg Ala Phe Lys Thr Lys Val Asp Phe Thr Lys
            355                 360                 365
Val Ser Val Pro Leu Asn Val Phe Arg His Ala Leu Glu Met Leu Ser
            370                 375                 380
Glu Gln Pro Gly Gly Phe Ile Ala Leu Asn Gly Phe Gly Gly Lys Met
385                 390                 395                 400
Ser Glu Ile Ser Thr Asp Phe Thr Pro Phe Pro His Arg Lys Gly Thr
                405                 410                 415
Lys Leu Met Phe Glu Tyr Ile Ile Ala Trp Asn Gln Asp Glu Glu Ser
                420                 425                 430
Lys Ile Gly Glu Phe Ser Glu Trp Leu Ala Lys Phe Tyr Asp Tyr Leu
            435                 440                 445
Glu Pro Phe Val Ser Lys Glu Pro Arg Val Gly Tyr Val Asn His Ile
450                 455                 460
Asp Leu Asp Ile Gly Gly Ile Asp Trp Arg Asn Lys Ser Ser Thr Thr
465                 470                 475                 480
Asn Ala Val Glu Ile Ala Arg Asn Trp Gly Glu Arg Tyr Phe Ser Ser
                485                 490                 495
```

Asn Tyr Glu Arg Leu Val Lys Ala Lys Thr Leu Ile Asp Pro Asn Asn
            500                 505                 510

Val Phe Asn His Pro Gln Ser Ile Pro Pro Met Met Lys Phe Glu Glu
            515                 520                 525

Ile Tyr Met Leu Lys Glu Leu
    530                 535

<210> SEQ ID NO 19
<211> LENGTH: 538
<212> TYPE: PRT
<213> ORGANISM: Eschscholzia californica

<400> SEQUENCE: 19

Met Glu Asn Lys Thr Pro Ile Phe Phe Ser Leu Ser Ile Phe Leu Ser
1               5                   10                  15

Leu Leu Asn Cys Ala Leu Gly Gly Asn Asp Leu Leu Ser Cys Leu Thr
            20                  25                  30

Phe Asn Gly Val Arg Asn His Thr Val Phe Ser Ala Asp Ser Asp Ser
            35                  40                  45

Asp Phe Asn Arg Phe Leu His Leu Ser Ile Gln Asn Pro Leu Phe Gln
    50                  55                  60

Asn Ser Leu Ile Ser Lys Pro Ser Ala Ile Ile Leu Pro Gly Ser Lys
65                  70                  75                  80

Glu Glu Leu Ser Asn Thr Ile Arg Cys Ile Arg Lys Gly Ser Trp Thr
                85                  90                  95

Ile Arg Leu Arg Ser Gly Gly His Ser Tyr Glu Gly Leu Ser Tyr Thr
            100                 105                 110

Ser Asp Thr Pro Phe Ile Leu Ile Asp Leu Met Asn Leu Asn Arg Val
            115                 120                 125

Ser Ile Asp Leu Glu Ser Glu Thr Ala Trp Val Glu Ser Gly Ser Thr
    130                 135                 140

Leu Gly Glu Leu Tyr Tyr Ala Ile Thr Glu Ser Ser Ser Lys Leu Gly
145                 150                 155                 160

Phe Thr Ala Gly Trp Cys Pro Thr Val Gly Thr Gly Gly His Ile Ser
                165                 170                 175

Gly Gly Gly Phe Gly Met Met Ser Arg Lys Tyr Gly Leu Ala Ala Asp
            180                 185                 190

Asn Val Val Asp Ala Ile Leu Ile Asp Ala Asn Gly Ala Ile Leu Asp
            195                 200                 205

Arg Gln Ala Met Gly Glu Asp Val Phe Trp Ala Ile Arg Gly Gly Gly
    210                 215                 220

Gly Gly Val Trp Gly Ala Ile Tyr Ala Trp Lys Ile Lys Leu Leu Pro
225                 230                 235                 240

Val Pro Glu Lys Val Thr Val Phe Arg Val Thr Lys Asn Val Ala Ile
                245                 250                 255

Asp Glu Ala Thr Ser Leu Leu His Lys Trp Gln Phe Val Ala Glu Glu
            260                 265                 270

Leu Glu Glu Asp Phe Thr Leu Ser Val Leu Gly Gly Ala Asp Glu Lys
            275                 280                 285

Gln Val Trp Leu Thr Met Leu Gly Phe His Phe Gly Leu Lys Thr Val
    290                 295                 300

Ala Lys Ser Thr Phe Asp Leu Leu Phe Pro Glu Leu Gly Leu Val Glu
305                 310                 315                 320

Glu Asp Tyr Leu Glu Met Ser Trp Gly Glu Ser Phe Ala Tyr Leu Ala
                325                 330                 335

```
Gly Leu Glu Thr Val Ser Gln Leu Asn Asn Arg Phe Leu Lys Phe Asp
            340                 345                 350

Glu Arg Ala Phe Lys Thr Lys Val Asp Leu Thr Lys Glu Pro Leu Pro
            355                 360                 365

Ser Lys Ala Phe Tyr Gly Leu Leu Glu Arg Leu Ser Lys Glu Pro Asn
            370                 375                 380

Gly Phe Ile Ala Leu Asn Gly Phe Gly Gly Gln Met Ser Lys Ile Ser
385                 390                 395                 400

Ser Asp Phe Thr Pro Phe Pro His Arg Ser Gly Thr Arg Leu Met Val
            405                 410                 415

Glu Tyr Ile Val Ala Trp Asn Gln Ser Glu Gln Lys Lys Lys Thr Glu
            420                 425                 430

Phe Leu Asp Trp Leu Glu Lys Val Tyr Glu Phe Met Lys Pro Phe Val
            435                 440                 445

Ser Lys Asn Pro Arg Leu Gly Tyr Val Asn His Ile Asp Leu Asp Leu
            450                 455                 460

Gly Gly Ile Asp Trp Gly Asn Lys Thr Val Val Asn Asn Ala Ile Glu
465                 470                 475                 480

Ile Ser Arg Ser Trp Gly Glu Ser Tyr Phe Leu Ser Asn Tyr Glu Arg
            485                 490                 495

Leu Ile Arg Ala Lys Thr Leu Ile Asp Pro Asn Asn Val Phe Asn His
            500                 505                 510

Pro Gln Ser Ile Pro Pro Met Ala Asn Phe Asp Tyr Leu Glu Lys Thr
            515                 520                 525

Leu Gly Ser Asp Gly Gly Glu Val Val Ile
            530                 535

<210> SEQ ID NO 20
<211> LENGTH: 542
<212> TYPE: PRT
<213> ORGANISM: Helianthus annuus

<400> SEQUENCE: 20

Met Asn Asn Ser Arg Ser Val Phe Leu Leu Val Leu Ala Leu Ser Phe
1               5                   10                  15

Cys Val Ser Phe Gly Ala Leu Ser Ser Ile Phe Asp Val Thr Ser Thr
            20                  25                  30

Ser Glu Asp Phe Ile Thr Cys Leu Gln Ser Asn Ser Asn Asn Val Thr
            35                  40                  45

Thr Ile Ser Gln Leu Val Phe Thr Pro Ala Asn Thr Ser Tyr Ile Pro
            50                  55                  60

Ile Trp Gln Ala Ala Ala Asp Pro Ile Arg Phe Asn Lys Ser Tyr Ile
65                  70                  75                  80

Pro Lys Pro Ser Val Ile Val Thr Pro Thr Asp Glu Thr Gln Ile Gln
            85                  90                  95

Thr Ala Leu Leu Cys Ala Lys Lys His Gly Tyr Glu Phe Arg Ile Arg
            100                 105                 110

Asp Gly Gly His Asp Phe Glu Gly Asn Ser Tyr Thr Ala Asn Ala Pro
            115                 120                 125

Phe Val Met Leu Asp Leu Val Asn Met Arg Ala Ile Glu Ile Asn Val
            130                 135                 140

Glu Asn Arg Thr Ala Leu Val Gln Gly Gly Ala Leu Leu Gly Glu Leu
145                 150                 155                 160

Tyr Tyr Thr Ile Ser Gln Lys Thr Asp Thr Leu Tyr Phe Pro Ala Gly
```

-continued

```
                165                 170                 175
Ile Trp Ala Gly Val Gly Val Ser Gly Phe Leu Ser Gly Gly Gly Tyr
            180                 185                 190
Gly Asn Leu Leu Arg Lys Tyr Gly Leu Gly Ala Asp Asn Val Leu Asp
        195                 200                 205
Ile Arg Phe Met Asp Val Asn Gly Asn Ile Leu Asp Arg Lys Ser Met
    210                 215                 220
Gly Glu Asp Leu Phe Trp Ala Leu Arg Gly Gly Ala Ser Ser Phe
225                 230                 235                 240
Gly Ile Val Leu Gln Trp Lys Leu Asn Leu Val Pro Val Pro Glu Arg
                245                 250                 255
Val Thr Leu Phe Ser Val Ser Tyr Thr Leu Glu Gln Gly Ala Thr Asp
            260                 265                 270
Ile Phe His Lys Tyr Gln Tyr Val Leu Pro Lys Phe Asp Arg Asp Leu
        275                 280                 285
Leu Ile Arg Val Gln Leu Asn Thr Glu Tyr Ile Gly Asn Thr Thr Gln
    290                 295                 300
Lys Thr Val Arg Ile Leu Phe His Gly Ile Tyr Gln Gly Asn Ile Asp
305                 310                 315                 320
Thr Leu Leu Pro Leu Leu Asn Gln Ser Phe Pro Glu Leu Asn Val Thr
                325                 330                 335
Arg Glu Val Cys Gln Glu Val Arg Met Val Gln Thr Thr Leu Glu Phe
            340                 345                 350
Gly Gly Phe Asn Ile Ser Thr Pro Thr Ser Val Leu Ala Asn Arg Ser
        355                 360                 365
Ala Ile Pro Lys Leu Ser Phe Lys Gly Lys Ser Asp Tyr Val Arg Thr
    370                 375                 380
Pro Ile Pro Arg Ser Gly Leu Arg Lys Leu Trp Arg Lys Met Phe Glu
385                 390                 395                 400
Asn Asp Asn Ser Gln Thr Leu Phe Met Tyr Thr Phe Gly Gly Lys Met
                405                 410                 415
Glu Glu Tyr Ser Asp Thr Ala Ile Pro Tyr Pro His Arg Ala Gly Val
            420                 425                 430
Leu Tyr Gln Val Phe Lys Arg Val Asp Phe Val Asp Gln Pro Ser Asp
        435                 440                 445
Lys Thr Leu Ile Ser Leu Arg Arg Leu Ala Trp Leu Arg Ser Phe Asp
    450                 455                 460
Lys Thr Leu Glu Pro Tyr Val Thr Ser Asn Pro Arg Glu Ala Tyr Met
465                 470                 475                 480
Asn Tyr Asn Asp Leu Asp Leu Gly Phe Asp Ser Ala Ala Tyr Glu Glu
                485                 490                 495
Ala Ser Glu Trp Gly Glu Arg Tyr Trp Lys Arg Glu Asn Phe Lys Lys
            500                 505                 510
Leu Ile Arg Ile Lys Ala Lys Val Asp Pro Glu Asn Phe Phe Arg His
        515                 520                 525
Pro Gln Ser Ile Pro Val Phe Ser Arg Pro Leu Ser Asp Met
    530                 535                 540

<210> SEQ ID NO 21
<211> LENGTH: 80
<212> TYPE: PRT
<213> ORGANISM: Raphanus sativus

<400> SEQUENCE: 21
```

-continued

```
Met Ala Lys Phe Ala Ser Ile Ile Val Leu Leu Phe Val Ala Leu Val
 1               5                  10                  15

Val Phe Ala Ala Phe Glu Glu Pro Thr Met Val Glu Ala Gln Lys Leu
            20                  25                  30

Cys Gln Arg Pro Ser Gly Thr Trp Ser Gly Val Cys Gly Asn Asn Asn
        35                  40                  45

Ala Cys Lys Asn Gln Cys Ile Arg Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 22
<211> LENGTH: 51
<212> TYPE: PRT
<213> ORGANISM: Sinapis alba

<400> SEQUENCE: 22

```
Gln Lys Leu Cys Glu Arg Pro Ser Gly Thr Trp Ser Gly Val Cys Gly
 1               5                  10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

<210> SEQ ID NO 23
<211> LENGTH: 80
<212> TYPE: PRT
<213> ORGANISM: Arabidopsis thaliana

<400> SEQUENCE: 23

```
Met Ala Lys Ser Ala Thr Ile Val Thr Leu Phe Phe Ala Ala Leu Val
 1               5                  10                  15

Phe Phe Ala Ala Leu Glu Ala Pro Met Val Val Glu Ala Gln Lys Leu
            20                  25                  30

Cys Glu Arg Pro Ser Gly Thr Trp Ser Gly Val Cys Gly Asn Ser Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 24
<211> LENGTH: 108
<212> TYPE: PRT
<213> ORGANISM: Helianthus annuus

<400> SEQUENCE: 24

```
Met Ala Lys Ile Ser Val Ala Phe Asn Ala Phe Leu Leu Leu Leu Phe
 1               5                  10                  15

Val Leu Ala Ile Ser Glu Ile Gly Ser Val Lys Gly Glu Leu Cys Glu
            20                  25                  30

Lys Ala Ser Gln Thr Trp Ser Gly Thr Cys Gly Lys Thr Lys His Cys
        35                  40                  45

Asp Asp Gln Cys Lys Ser Trp Glu Gly Ala Ala His Gly Ala Cys His
    50                  55                  60

Val Arg Asp Gly Lys His Met Cys Phe Cys Tyr Phe Asn Cys Ser Lys
```

```
                        65                  70                  75                  80
Ala Gln Lys Leu Ala Gln Asp Lys Leu Arg Ala Glu Leu Ala Lys
                    85                  90                  95

Glu Lys Ile Glu Pro Glu Lys Ala Thr Ala Lys Pro
            100                 105
```

<210> SEQ ID NO 25
<211> LENGTH: 100
<212> TYPE: PRT
<213> ORGANISM: Pisum Sativum

<400> SEQUENCE: 25

```
Met Glu Lys Lys Ser Leu Ala Ala Leu Ser Phe Leu Leu Leu Val
 1               5                  10                  15

Leu Phe Val Ala Gln Glu Ile Val Thr Glu Ala Asn Thr Cys Glu
                20                  25                  30

His Leu Ala Asp Thr Tyr Arg Gly Val Cys Phe Thr Asn Ala Ser Cys
                35                  40                  45

Asp Asp His Cys Lys Asn Lys Ala His Leu Ile Ser Gly Thr Cys His
        50                  55                  60

Asp Trp Lys Cys Phe Cys Thr Gln Asn Cys Glu Arg Arg Asn Lys
65                  70                  75                  80

Asn Trp Asn Asp Cys Met Glu Asn Thr Pro Arg Pro Glu Arg Thr Tyr
                85                  90                  95

Asn Ala Met Glu
            100
```

<210> SEQ ID NO 26
<211> LENGTH: 26
<212> TYPE: DNA
<213> ORGANISM: Artificial Sequence
<220> FEATURE:
<223> OTHER INFORMATION: PCR primer corresponding to vector sequence

<400> SEQUENCE: 26
gcgattaagt tgggtaacgc caggqt                                          26

<210> SEQ ID NO 27
<211> LENGTH: 26
<212> TYPE: DNA
<213> ORGANISM: Artificial Sequence
<220> FEATURE:
<223> OTHER INFORMATION: PCR primer corresponding to vector sequence

<400> SEQUENCE: 27
tccggctcgt atgttgtgtg gaattg                                          26

<210> SEQ ID NO 28
<211> LENGTH: 230
<212> TYPE: DNA
<213> ORGANISM: Helianthus annuus
<220> FEATURE:
<221> NAME/KEY: misc_feature
<222> LOCATION: (1)...(230)
<223> OTHER INFORMATION: n = A,T,C or G

<400> SEQUENCE: 28
tgatcagttt tgtacacggt gcaagggtta ttgcacccgc cagagcccgt aactcnccag      60
gacactggcc attgatatcc gcagtacatg agataccccg ggtgcaccca ttagaattgg     120
gtctaaacac catcggcaca ttgaatccgt ccacaagaga aatgtcaaag aaatcaagat     180

-continued

```
tgttgaactg gttccaagcg tactcggccc atgtgtttgg gtggggtacc          230
```

<210> SEQ ID NO 29
<211> LENGTH: 20
<212> TYPE: DNA
<213> ORGANISM: Helianthus annuus

<400> SEQUENCE: 29

```
ccgagtacgc tttaaccagt                                            20
```

<210> SEQ ID NO 30
<211> LENGTH: 21
<212> TYPE: DNA
<213> ORGANISM: Helainthus annuus

<400> SEQUENCE: 30

```
tccgcagtac atgagatacc c                                          21
```

<210> SEQ ID NO 31
<211> LENGTH: 29
<212> TYPE: DNA
<213> ORGANISM: Helianthus annuus

<400> SEQUENCE: 31

```
acaatgacaa cctccaccct tcccacttt                                  29
```

<210> SEQ ID NO 32
<211> LENGTH: 112
<212> TYPE: DNA
<213> ORGANISM: Helianthus annuus

<400> SEQUENCE: 32

```
tccggaccat gtctggcttg ccttctcaca taattctcct ttcaccgatc cgatttctga    60
gatagcaaga acaaagagaa gcagaagaaa agcattgaaa gcaactgaaa tt           112
```

<210> SEQ ID NO 33
<211> LENGTH: 26
<212> TYPE: DNA
<213> ORGANISM: Helianthus annuus

<400> SEQUENCE: 33

```
gaccatgtct ggcttgcctt ctcaca                                     26
```

<210> SEQ ID NO 34
<211> LENGTH: 35
<212> TYPE: DNA
<213> ORGANISM: Helianthus annuus

<400> SEQUENCE: 34

```
gagcttgagc ttagttcagt aacttaaaaa tggcc                           35
```

<210> SEQ ID NO 35
<211> LENGTH: 163
<212> TYPE: DNA
<213> ORGANISM: Helianthus annuus

<400> SEQUENCE: 35

```
tgtacacatt tggtgggaag atggaggagt actcagatac agcaattccg tatccccata    60
gagctggggt gttgtaccaa gtgttcaaga gggtggactt cgtggatcag ccttcggaca   120
agaccttgat atcactcaga cggttggctt ggctccgaag ctt                    163
```

-continued

```
<210> SEQ ID NO 36
<211> LENGTH: 24
<212> TYPE: DNA
<213> ORGANISM: Helianthus annuus

<400> SEQUENCE: 36
ccaaccgtct gagtgatatc aagg                                              24

<210> SEQ ID NO 37
<211> LENGTH: 24
<212> TYPE: DNA
<213> ORGANISM: Helianthus annuus

<400> SEQUENCE: 37
gggaagatgg aggagtactc agat                                              24

<210> SEQ ID NO 38
<211> LENGTH: 29
<212> TYPE: DNA
<213> ORGANISM: Helianthus annuus

<400> SEQUENCE: 38
cggcacgagt aactctcgtt cagtgttcc                                         29

<210> SEQ ID NO 39
<211> LENGTH: 22
<212> TYPE: DNA
<213> ORGANISM: Artificial Sequence
<220> FEATURE:
<223> OTHER INFORMATION: PCR primer corresponding to vector sequence

<400> SEQUENCE: 39
gtaatacgac tcactatagg gc                                                22

<210> SEQ ID NO 40
<211> LENGTH: 26
<212> TYPE: DNA
<213> ORGANISM: Helianthus annuus

<400> SEQUENCE: 40
cgaatagtga acacggctgc attggt                                            26

<210> SEQ ID NO 41
<211> LENGTH: 26
<212> TYPE: DNA
<213> ORGANISM: Helianthus annuus

<400> SEQUENCE: 41
gctgcagctt gccaaatggg tatgta                                            26
```